United States Patent
Gao et al.

(10) Patent No.: US 12,171,179 B2
(45) Date of Patent: Dec. 24, 2024

(54) METHODS AND COMPOSITIONS TO INCREASE YIELD THROUGH MODIFICATIONS OF FEA3 GENOMIC LOCUS AND ASSOCIATED LIGANDS

(71) Applicant: PIONEER HI-BRED INTERNATIONAL, INC., Johnston, IA (US)

(72) Inventors: Huirong Gao, Johnston, IA (US); Zhenglin Hou, Ankeny, IA (US); Robert B Meeley, Des Moines, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 465 days.

(21) Appl. No.: 17/260,408

(22) PCT Filed: Jul. 17, 2019

(86) PCT No.: PCT/US2019/042148
§ 371 (c)(1),
(2) Date: Jan. 14, 2021

(87) PCT Pub. No.: WO2020/023258
PCT Pub. Date: Jan. 30, 2020

(65) Prior Publication Data
US 2022/0346341 A1    Nov. 3, 2022

Related U.S. Application Data

(60) Provisional application No. 62/702,237, filed on Jul. 23, 2018.

(51) Int. Cl.
*A01H 6/46* (2018.01)
*A01H 5/10* (2018.01)
*C12N 15/82* (2006.01)

(52) U.S. Cl.
CPC ............. *A01H 6/4684* (2018.05); *A01H 5/10* (2013.01); *C12N 15/8261* (2013.01)

(58) Field of Classification Search
None
See application file for complete search history.

(56) References Cited

U.S. PATENT DOCUMENTS

| | | |
|---|---|---|
| 7,179,963 B2 | 2/2007 | Bruce et al. |
| 9,701,979 B2 | 7/2017 | Allen et al. |
| 10,584,349 B2 | 3/2020 | Allen et al. |
| 11,643,665 B2 | 5/2023 | Allen et al. |
| 2007/0011783 A1 | 1/2007 | Liu et al. |
| 2007/0020908 A1 | 1/2007 | Honer et al. |
| 2007/0209085 A1 | 9/2007 | Wu et al. |
| 2014/0359836 A1 | 12/2014 | Wu et al. |
| 2015/0047071 A1 | 2/2015 | Allen et al. |
| 2017/0275642 A1 | 9/2017 | Allen et al. |

FOREIGN PATENT DOCUMENTS

| | | | |
|---|---|---|---|
| WO | 0170987 A2 | 9/2001 | |
| WO | WO-2013138408 A1 * | 9/2013 | ............... A01H 5/10 |
| WO | 2018/071362 A1 | 4/2018 | |

OTHER PUBLICATIONS

Fasciated ear3 [*Zea mays*], National Library of Medicine, https://www.ncbi.nlm.nih.gov/protein/ONM30618.1?report=genbank&log$=protalign&blast_rank=2&RID=T47NKVBW01N, Published Online Feb. 6, 2017 (Year: 2017).*
Je, Byoung II, et al. "Signaling from maize organ primordia via Fasciated EAR3 regulates stem cell proliferation and yield traits." Nature genetics 48.7 (2016): 785-791. (Year: 2016).*
Zong, Yuan, et al. "Precise base editing in rice, wheat and maize with a Cas9-cytidine deaminase fusion." Nature biotechnology 35.5 (2017): 438-440. (Year: 2017).*
Licht, Mark. "Estimating corn yields using yield components." (2017). (Year: 2017).*
Zhao, Lin-Yong, et al. "Mapping the epigenetic modifications of DNA and RNA." Protein & cell 11.11 (2020): 792-808. (Year: 2020).*
Je, Signaling from maize organ primordia via Fasciated EAR3 regulates stem cell proliferation and yield traits, Nature Genetics, May 16, 2016 (Year: 2016).*
Licht, Estimating Corn Yields Using Yield Components, Iowa State University Integrated Crop Management, Aug. 21, 2017 (Year: 2017).*
Jung, Christian, and Andreas E. Müller. "Flowering time control and applications in plant breeding." Trends in plant science 14.10 (2009): 563-573. (Year: 2009).*
Eid, et al: "CRISPR base editors: genome editing without double-stranded breaks," Biochem J, Jun. 11, 2018 (Jun. 11, 2018), vol. 475, pp. 1955-1964.
International Search Report and Written Opinion for International Application No. PCT/US2019/042148, Mailed Oct. 17, 2019.
Benfey P.N., et al., "The Cauliflower Mosaic Virus 35S Promoter: Combinatorial Regulation of Transcription in Plants," Science, Nov. 16, 1990, vol. 250, pp. 959-966, 9 Pages.
Bommert P., et al., "Thick Tassel Dwarf1 Encodes a Putative Maize Ortholog of the Arabidopsis CLAVATA1 Leucine-Rich Repeat Receptor-Like Kinase," Development, 2005, vol. 132, pp. 1235-1245.
Bommert P., "Isolation and Analyse der Mutation Thick Tassel Dwarf1 Aus *Zea mays*," Dec. 31, 2003, pp. 8-78.
Brucker G., et al., "Targeted Site-Directed Mutagenesis of a HemeOxygenase Locus by Gene Replacement in the Moss *Ceratodon purpureus*," Planta, 2005, vol. 220, pp. 864-874.
Fletcher J.C., et al., "Signaling of Cell Fate Decisions by Clavata3 in *Arabidopsis* Shoot Meristems," Science, Mar. 19, 1999, vol. 283, pp. 1911-1914.

(Continued)

*Primary Examiner* — Weihua Fan
*Assistant Examiner* — Brian James Sullivan

(57) ABSTRACT

Methods and compositions for modulating plant meristems. Methods are provided for modulating fea3 and/or Fcp1 genomic locus in a host plant or plant cell to improve agronomic characteristics such as kernel number.

6 Claims, 5 Drawing Sheets

Figure 1:
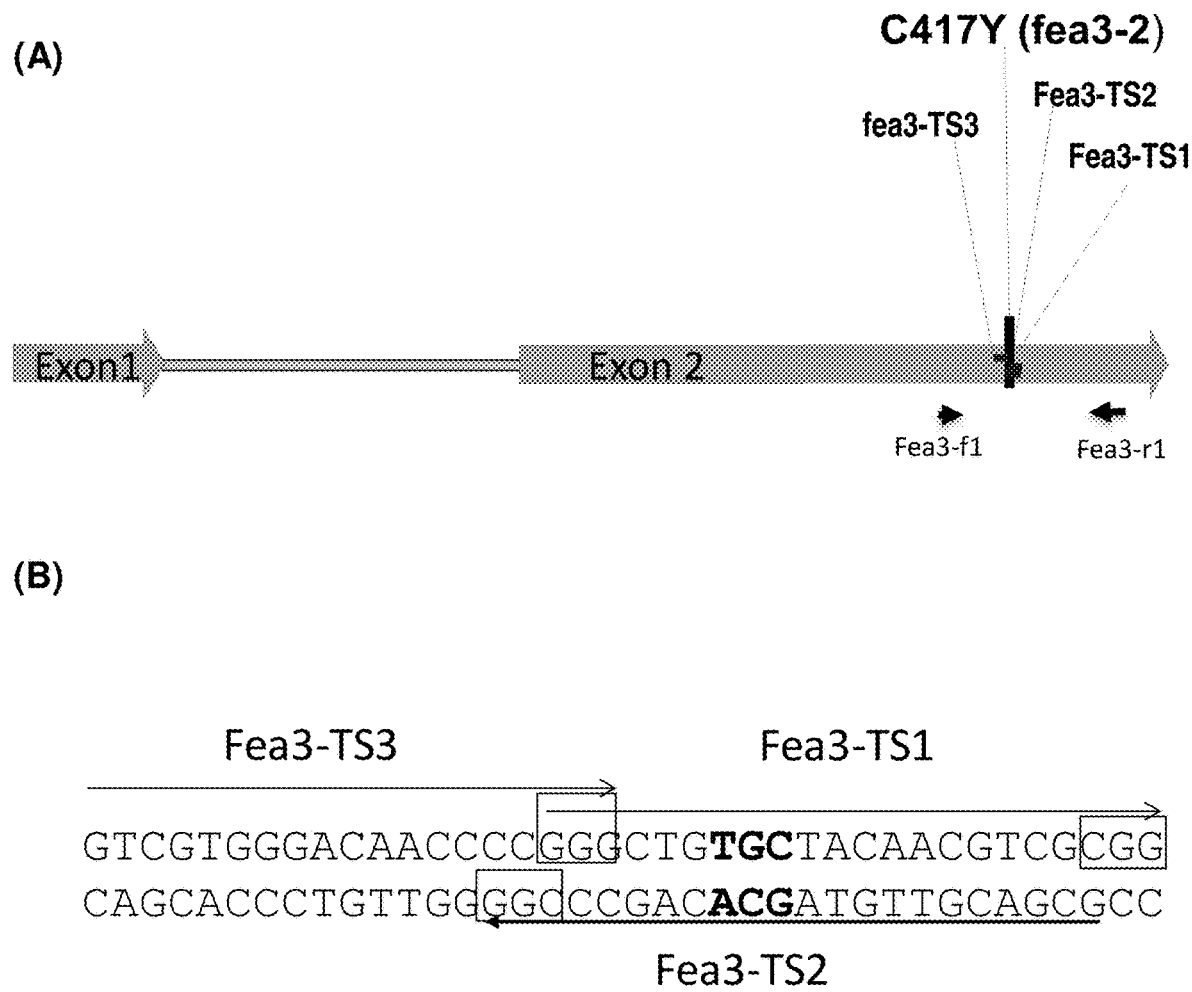

Specification includes a Sequence Listing.

(56) References Cited

OTHER PUBLICATIONS

International Preliminary Report on Patentability for International Application No. PCT/US2013/030672, mailed Sep. 25, 2014, 6 Pages.
International Preliminary Report on Patentability for International Application No. PCT/US2019/042148, mailed Feb. 4, 2021, 17 Pages.
International Search Report and Written Opinion for International Application No. PCT/US2013/030672, mailed Jun. 26, 2013, 09 Pages.
Jackson D., et al., "The Genetics of Ear Fasciation in Maize," Maize Newsletters, Dec. 31, 1998, vol. 38, No. 2, pp. 1-2.
Mccallum., et al., Plant Physiology, 2000, vol. 123, pp. 439-442.
Mertens T.R., et al., "The Morphology, Anatomy, and Genetics of a Stem Fasciation in Lycopersicon Esculentum," American Journal of Botany, Nov. 1954, vol. 41, No. 9, pp. 726-732.
Szymkowiak E.J., et al., "The Internal Meristem Layer (L3) Determines Floral Meristem Size and Carpel Number in Tomato Periclinal Chimeras," The Plant Cell, Sep. 1992, vol. 4, pp. 1089-1100.
Taguchi-Shiobara F., et al., "The Fasciated Ear2 Gene Encodes a Leucine-Rich Repeat Receptor-Like Protein that Regulates Shoot Meristem Proliferation in Maize," Genes & Development, Dec. 31, 2001, vol. 15, pp. 2755-2766.
Tiedemann J., et al., "Dissection of a Complex Seed Phenotype: Novel Insights of FUSCA3 Regulated Developmental Processes," Developmental Biology, Epub Feb. 13, 2008, May 1, 2008, vol. 317, No. 1, pp. 1-12.
Trotochaud A.E., et al., "The CLAVATA1 Receptor-Like Kinase Requires CLAVATA3 for its Assembly into a Signaling Complex that Includes KAPP and a Rho-Related Protein," The Plant Cell, Mar. 1999, vol. 11, pp. 393-405.
UNIPROT: Database Accession No. Q5PP26_ARATH, Jan. 4, 2005, 3 pages.
UniProt ID No. C5XEW7_SORBI, Sep. 1, 2009.
UniProt ID No. C5XEWS_SORBI, Sep. 1, 2009.
UniProt ID No. F4JA38_ARATH, Jun. 28, 2011.
UniProt ID No. I1K192_SOYBN, Jun. 13, 2012.
UniProt ID No. I1MUH6_SOYBN, Jun. 13, 2012.
UniProt ID No. I1NHK5_SOYBN, Jun. 13, 2012.
UniProt ID No. K7K2T2_SOYBN, Jan. 9, 2013.
UniProt ID No. K7K7H6_SOYBN, Jan. 9, 2013.
UniProt ID No. K7LKJ4_SOYBN, Jan. 9, 2013.
UniProt ID No. PII2ARATH, Feb. 5, 2008.
UniProt ID No. q0dgx0_orysj Oct. 17, 2006.
UniProt ID No. Q9A41ARATH, Jun. 1, 2001.
UNIPROT: ID Q9CA41_ARATH, "SubName: Full=At1g68780 {ECO:0000313|EMBL:AAU90067.1}," Jun. 1, 2001, 2 Pages.
Vollbrecht E., et al., "Development of the Inflorescences," Handbook of Maize: Its Biology, Dec. 31, 2009, pp. 13-40.
Wang Y., et al., "Genes Controlling Plant Architecture," Current Opinion in Biotechnology, Apr. 2006, vol. 17, No. 2, pp. 123-129, ISSN 0958-1669, XP024962866.
Yamamoto E., et al., "Molecular Characterization of Two Soybean Homologs of *Arabidopsis thaliana* CLAVATA1 From the Wild Type and Fasciation Mutant," Biochimica et Biophysica Acta, 2000, vol. 1491, pp. 333-340.

\* cited by examiner

```
                                        Cys
Fea3-TS3   GTCGTGGGACAACCCCGGGCTGTGCTACAACGTCGCGG
           CAGCACCCTGTTGGGGCCCGACACGATGTTGCAGCGCC

Tyr
           GTCGTGGGACAACCCCGGtCTGTACTACAACGTCGCGG    Repair template 1

GTCGTGGGAtAACCCaGGtCTGTACTACAACGTCGCGG    Repair template 2

GTCGTGGGAtAACCCaGGGCTGTACTACAACGTCGCGG    Repair template 3

Fea3-TS2   GTCGTGGGACAACCCCGGGGCTGTGCTACAACGTCGCGG
           CAGCACCCTGTTGGGGCCCCGACACGATGTTGCAGCGCC

GTCGTGGGACAACCCaGGGCTGTACTACAACGTCGCGG    Repair template 1
           GTCGTGGGACAACCCaGGGCTGTACTAtAACGTaGCGG    Repair template 2
```

FIG. 2

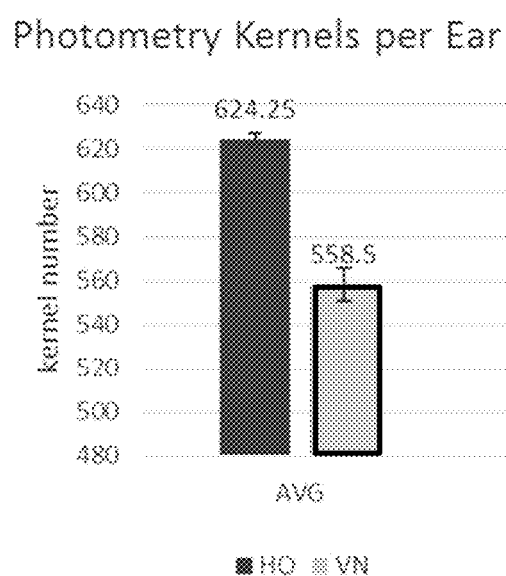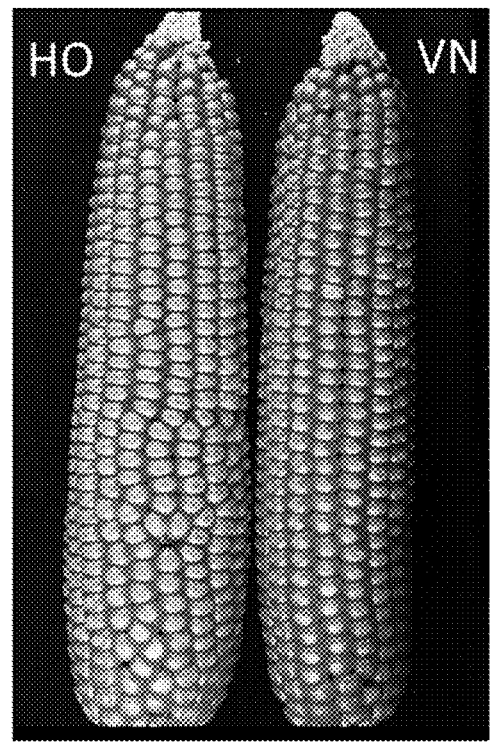
FIG. 3

(A)

```
rep1   LWYPTVMSIGPVLDN-SLQCG-PD-AKF-SAQL----F-D
rep2   -----LRRLRTLSEYSCFPASNPTAIPTGSWEKL---A-G
rep3   -T----LETLE-FRTNPGLN-G-AIPA----S--L----GRL
rep4   AS----LQSLV-LVEN-NLT-G-PVPA----E--L----G-A
rep5   LSR---LRRLV-LSGN-GLS-G-PIPV----T--L----GNDR
rep6   RADELLLIVD-LSRN-VLT-G-SLPS----S--L----G-G
rep7   LTG---LLKMD-LSSN-LLQ-G-SIPP----E--L----A-G
rep8   LRS---LTLLD-LRNN-SLT-G-GLPQ----F--V----Q-G
rep9   MAS---LQDLL-LSNN-PLG-G-GLPQ----S--G----WGA
rep10  LAG---LATLD-LSNV-GLV-G-AIPG----S--M----A-A
rep11  LTG---LRELA-LDHN-RLT-G-AVPP----E--L----ARL
rep12  PS----IGALY-LNGN-NLT-G-TLEF----SAGFYQRM-G
              LxxLx  LxxN  xL
```

(B)

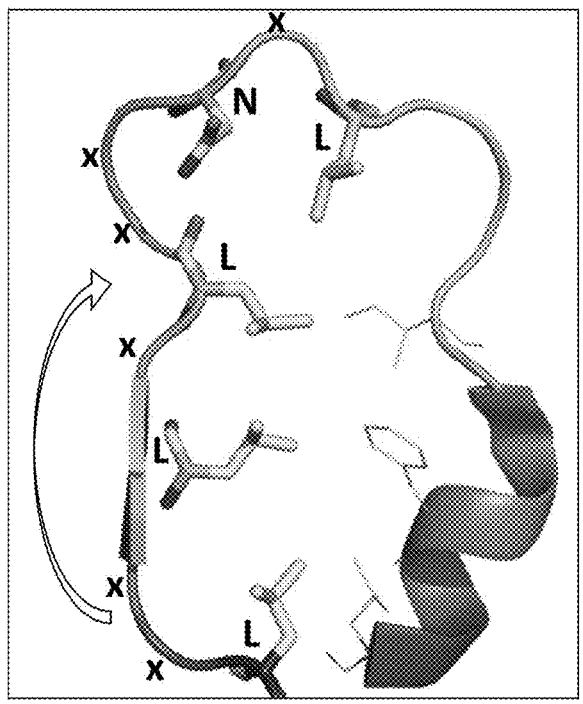

FIG. 4

METHODS AND COMPOSITIONS TO INCREASE YIELD THROUGH MODIFICATIONS OF FEA3 GENOMIC LOCUS AND ASSOCIATED LIGANDS

CROSS-REFERENCE TO RELATED APPLICATIONS

This application is a 371 National Stage Entry of PCT Application No. PCT/US19/42148, filed 17 Jul. 2019, which claims the benefit of U.S. Provisional Patent Application Ser. No. 62/702,237, filed 23 Jul. 2018, all of which are herein incorporated by reference in its their entireties.

FIELD

The disclosure relates to the field of the genetic manipulation of plants, particularly the modulation of gene activity and development in plants.

REFERENCE TO SEQUENCE LISTING SUBMITTED ELECTRONICALLY

The official copy of the sequence listing is submitted electronically via EFS-Web as an ASCII formatted sequence listing with a file named "7791WOPCT_ST25.txt" created on Jul. 15, 2019 and having a size of 48 kilobytes and is filed concurrently with the specification. The sequence listing contained in this ASCII formatted document is part of the specification and is herein incorporated by reference in its entirety.

BACKGROUND

Leaves and the axillary meristems that generate branches and flowers are initiated in regular patterns from the shoot apical meristem (SAM). The cells of the shoot apical meristem summit serve as stem cells that divide to continuously displace daughter cells to the surrounding regions, where they are incorporated into differentiated leaf or flower primordia. The meristems are thus capable of regulating their size during development by balancing cell proliferation with the incorporation of cells into new primordia. The SAM provides all aerial parts of plant body. It is desirable to be able to control the size and appearance of shoot and floral meristems, to give increased yields of leaves, flowers, and fruit. Novel methods and compositions for the modulation of meristem development to improve agronomic characteristics such as kernel number and yield are provided herein.

SUMMARY

In an embodiment, a method of producing a modified plant with an altered activity and/or expression of an endogenous fea3 gene, includes:
  a. providing a guide RNA that targets fea3 genomic locus and a Cas endonuclease that creates a DNA break at the fea3 genomic locus in association with the guide RNA;
  b. generating the modified plant wherein the plant expresses altered fea3 activity and/or expression compared to a control plant.
2. In an embodiment, a method of producing a modified plant with alteration of an agronomic characteristic, the method includes:
  a. providing a guide RNA that targets fea3 genomic locus and a Cas endonuclease that creates a DNA break at the fea3 genomic locus in association with the guide RNA;
  b. generating a population of modified plants comprising one or more modifications at the fea3 genomic locus; and
  c. selecting the modified plant of (b), wherein the modified plant exhibits an alteration of at least one agronomic characteristic selected from the group consisting of: ear meristem size, kernel row number, leaf number, inflorescence number, branching within the inflorescence, flower number, fruit number, seed number, root branching, root biomass, root lodging, biomass, yield and a combination thereof, when compared to a control plant not comprising the modification.

In an embodiment, a method of identifying a weak allele of fea3, the method includes:
  a. introducing one or more site directed DNA breaks at a genomic locus comprising fea3 through guide RNA associated Cas endonuclease;
  b. identifying one or more mutant plants that exhibit a weak fea3 phenotype than a fea3 null plant; and
  c. identifying the weak fea3 allele from the mutant plant with weaker fea3 phenotype.

In an embodiment, a plant in which expression of the endogenous fea3 gene or the activity of the encoded FEA3 polypeptide is altered relative to a control plant, wherein such alteration is a result of introducing a site-specific genomic modification at the endogenous fea3 gene by a targeted endonuclease. In an embodiment, the expression and/or the activity of the endogenous FEA3 polypeptide is altered by one or more modification selected from the group consisting of:
  (a) reduced expression of a polynucleotide encoding the FEA3 polypeptide;
  (b) reduced activity of the FEA3 polypeptide;
  (c) generation of one or more alternative spliced transcripts of a polynucleotide encoding the fea3 polypeptide;
  (d) deletion of one or more domains of the FEA3 polypeptide;
  (e) frameshift mutation in one or more exons of a polynucleotide encoding the fea3 polypeptide;
  (f) deletion of a substantial portion of the polynucleotide encoding the fea3 polypeptide or deletion of the polynucleotide encoding the FEA3 polypeptide;
  (g) repression of an enhancer motif present within a regulatory region encoding the fea3 polypeptide;
  (h) modification of one or more nucleotides or deletion of a regulatory element operably linked to the expression of the polynucleotide encoding the FEA3 polypeptide, wherein the regulatory element is present within a promoter, intron, 3'UTR, terminator or a combination thereof;
  (i) mutation in or near the Leucine Rich Repeat (LRR) domain of FEA3 polypeptide; and
  (j) mutation in or near the domain of fea3 exposed to extracellular signaling factors involved in the development of organ primordia.

A method of making a plant that is modified, the method comprising the steps of
  a. introducing a genomic modification into the endogenous Fea3 gene; and
  b. detecting the mutation.
In an embodiment, the genomic modification is introduced by guide RNA associated Cas9, guide RNA associated Cpf1 or any other CRISPR-associated endonuclease systems, TALEN, zinc finger endonucleases, and site-specific meganucleases.

In an embodiment, a method of producing a modified maize plant with an alteration in agronomic characteristic, the method includes:
  a. introducing into a regenerable plant cell a guide RNA, Cas endonuclease such that the guide RNA targets an endogenous genomic locus that encodes a polypeptide having an amino acid sequence that is at least 90% identical to SEQ ID NOS: 21-24
  b. regenerating a modified plant from the regenerable plant cell after step (a), wherein the modified plant comprises in its genome one or more modifications at the endogenous genomic locus; and
  c. selecting a modified plant of (b), wherein the modified plant exhibits an alteration in at least one agronomic characteristic selected from the group consisting of: enlarged ear meristem, kernel row number, seed number, root branching, root biomass, root lodging, biomass and yield, when compared to a control plant not comprising the one or more modifications.

In an embodiment, a plant is selected from the group consisting of: *Arabidopsis*, tomato, maize, soybean, sunflower, sorghum, canola, wheat, alfalfa, cotton, rice, barley, millet, sugar cane and switchgrass.

In an embodiment, a guide RNA targets an endogenous genomic locus that encodes a polypeptide comprising an amino acid sequence that is at least 90% identical to SEQ ID NOS: 21-24.

In an embodiment, a DNA construct includes a polynucleotide that produces the guide RNA to target fea3 and/or Fcp1 genomic locus. In an embodiment, a plant cell includes the guide RNA described herein. In an embodiment, the plant cell includes a Cas endonuclease. In an embodiment, seeds produced from the modified plants described herein also contain one or more of the mutations targeting the endogenous fea3 genomic locus.

In an embodiment, a method of generating weak alleles of fea3 and/or Fcp1 in a population of maize plants, the method comprises introducing one or more modifications at a genomic locus encoding a fea3 polypeptide having an amino acid sequence that is at least 95% identical to SEQ ID NOS: 21-24 by a site-specific DNA break agent and identifying weak alleles of fea3 by evaluating an improvement in one or more agronomic characteristics selected from the group consisting of: ear meristem size, kernel row number, leaf number, inflorescence number, branching within the inflorescence, flower number, fruit number, seed number, root branching, root biomass, root lodging, biomass, yield and a combination thereof, when compared to a control plant not comprising the modification.

In an embodiment, the site-specific DNA break agent is selected from the group consisting of: guide RNA associated Cas9, guide RNA associated Cpf1, CRISPR-associated endonuclease systems, TALEN, zinc finger endonucleases, and a site-specific meganuclease. In an embodiment, the population of maize plants is a hybrid and the agronomic characteristic is an increase in kernel number.

The disclosure includes a recombinant DNA construct comprising an isolated polynucleotide of the current disclosure operably linked, in sense or antisense orientation, to a promoter that is shoot apical meristem specific or shoot apical meristem preferred.

This disclosure includes a vector, cell, plant, or seed comprising any of the recombinant DNA constructs described in the present disclosure. The disclosure encompasses plants produced by the methods described herein.

The disclosure also encompasses regenerated, mature and fertile modified plants comprising the recombinant DNA constructs described above, modified seeds produced therefrom, T1 and subsequent generations. The modified plant cells, tissues, plants, and seeds may comprise at least one recombinant DNA construct of interest. In one embodiment, the plant is selected from the group consisting of: *Arabidopsis*, tomato, maize, soybean, sunflower, sorghum, canola, wheat, alfalfa, cotton, rice, barley, millet, sugar cane and switchgrass.

A plant in which expression of the endogenous Fcp1 gene or the activity of the encoded Fcp1 polypeptide is altered relative to a control plant, wherein such alteration is a result of introducing a site-specific genomic modification at the endogenous Fcp1 gene by a targeted endonuclease.

In an embodiment, the expression and/or the activity of the endogenous Fcp1 polypeptide is altered by one or more modification selected from the group consisting of:
  (a) reduced expression of a polynucleotide encoding the Fcp1 polypeptide;
  (b) reduced activity of the Fcp1 polypeptide;
  (c) generation of one or more alternative spliced transcripts of a polynucleotide encoding the Fcp1 polypeptide;
  (d) a point mutation resulting in a modification of one or more amino acids of SEQ ID NO: 34 or a sequence that is at least 90%-99% identical to SEQ ID NO: 34;
  (e) frameshift mutation in one or more exons of a polynucleotide encoding the Fcp1 polypeptide;
  (f) deletion of a substantial portion of the polynucleotide encoding the fea3 polypeptide or deletion of the polynucleotide encoding the Fcp1 polypeptide;
  (g) repression of an enhancer motif present within a regulatory region encoding the Fcp1 polypeptide;
  (h) modification of one or more nucleotides or deletion of a regulatory element operably linked to the expression of the polynucleotide encoding the Fcp1 polypeptide, wherein the regulatory element is present within a promoter, intron, 3'UTR, terminator or a combination thereof;
  (i) mutation in or near a residue involved in interaction of the Fcp1 polypeptide with one or more of the Leucine Rich Repeat (LRR) domains of fea3 polypeptide; and
  (j) mutation in or near a region of Fcp1 ligand exposed to extracellular signaling factors involved in the development of organ primordia.

In one embodiment, the plant comprising the recombinant constructs described in the present disclosure is a monocotyledonous plant. In another embodiment, the plant comprising the recombinant constructs described in the present disclosure is a maize plant.

In an embodiment, methods include providing at least one polynucleotide modification template, wherein said polynucleotide modification template is used to generate a modified fea3 genomic locus. In an embodiment, methods include providing at least one polynucleotide modification template, wherein said polynucleotide modification template is used to generate a modified genomic locus comprising Fcp1. In an embodiment, the alteration is a result of introducing a site-specific genomic modification at the endogenous fea3 gene by the targeted endonuclease and at least one polynucleotide modification template, wherein said polynucleotide modification template is used to generate a modified fea3 gene. In an embodiment, the genomic modification is introduced by guide RNA associated Cas9, guide RNA associated Cpf1 or any other CRISPR-associated endonuclease systems, and at least one polynucleotide modification template, wherein said polynucleotide modification template is used to generate a modified fea3 genomic locus, modified ZmFCP1 locus, or a combination of the foregoing. In an embodiment, the methods include providing at least one polynucleotide modification template, wherein said polynucleotide modification template is used to generate the modified genomic locus that encodes a polypeptide having an amino acid sequence that is at least 90% identical to SEQ ID NOS: 21-24.

In an embodiment, the methods include providing at least one polynucleotide modification template when the site-specific agent is a guide RNA associated Cas9, guide RNA associated Cpf1, or CRISPR-associated endonuclease systems, wherein said polynucleotide modification template is used to generate a modified genomic locus encoding a FEA3 polypeptide having an amino acid sequence that is at least 95% identical to SEQ ID NOS: 21-24.

BRIEF DESCRIPTION OF THE DRAWINGS AND SEQUENCE LISTINGS

The disclosure can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 1 shows schematic of the fea3 gene with fea3-2 position and the three target sites' location (A) and target site relative locations to edit position of C417 (TGC) on fea3 gene exon 2 (B). Arrow indicates the target from start to PAM (inside rectangle), the C417 code of TGC is in bold. Fea3-TS3 (SEQ ID NO: 3), Fea3-TS1 (SEQ ID NO: 1) and Fea3-TS2 (SEQ ID NO: 2) are shown in (B).

FIG. 2 shows oligo repair templates with edits and SNPs for editing fea3 genomic locus. Guide sequence is in italic, PAM sequence is shown inside the rectangle, C417 and 417Y sequences are in bold, underline indicates the point mutation for C417Y, bold lowercase indicates additional SNPs in the repair oligo templates. SEQ ID NO: 29—Repair template 1 (Fea3-TS3); SEQ ID NO: 30—Repair template 2 (Fea3-TS3); SEQ ID NO: 31—Repair template 3 (Fea3-TS3); SEQ ID NO: 32—Repair template 1 (Fea3-TS2); SEQ ID NO: 33Repair template 2 (Fea3-TS2); and Fea3-TS3 (SEQ ID NO: 3) target.

FIG. 3 shows kernels per ear of homozygous fea3-2 edited maize plants and the image of genome edited fea3-2 ear vs. control variant null segregant (VN).

FIG. 4 shows alignment of the 12 predicted leucine rich repeats (LRR) (SEQ ID NOS: 35-46, in the order of sequences appearing from rep1 to rep12) of the maize Fea3 protein (A) and a model representation of a typical LRR repeat unit (B). The conserved Leucine rich region is shown below the alignment box. The circled residues shown within the alignment are representative targets for changing the amino acid residues. The numbers for LRR repeat units correspond to the amino acid positions present in Fea3 protein as noted by SEQ ID NO: 23—R127, R128, R130, F134, R164, R208, R209, R242, Y244, K261, R357, F358, H363, Y384.

Figure 5:
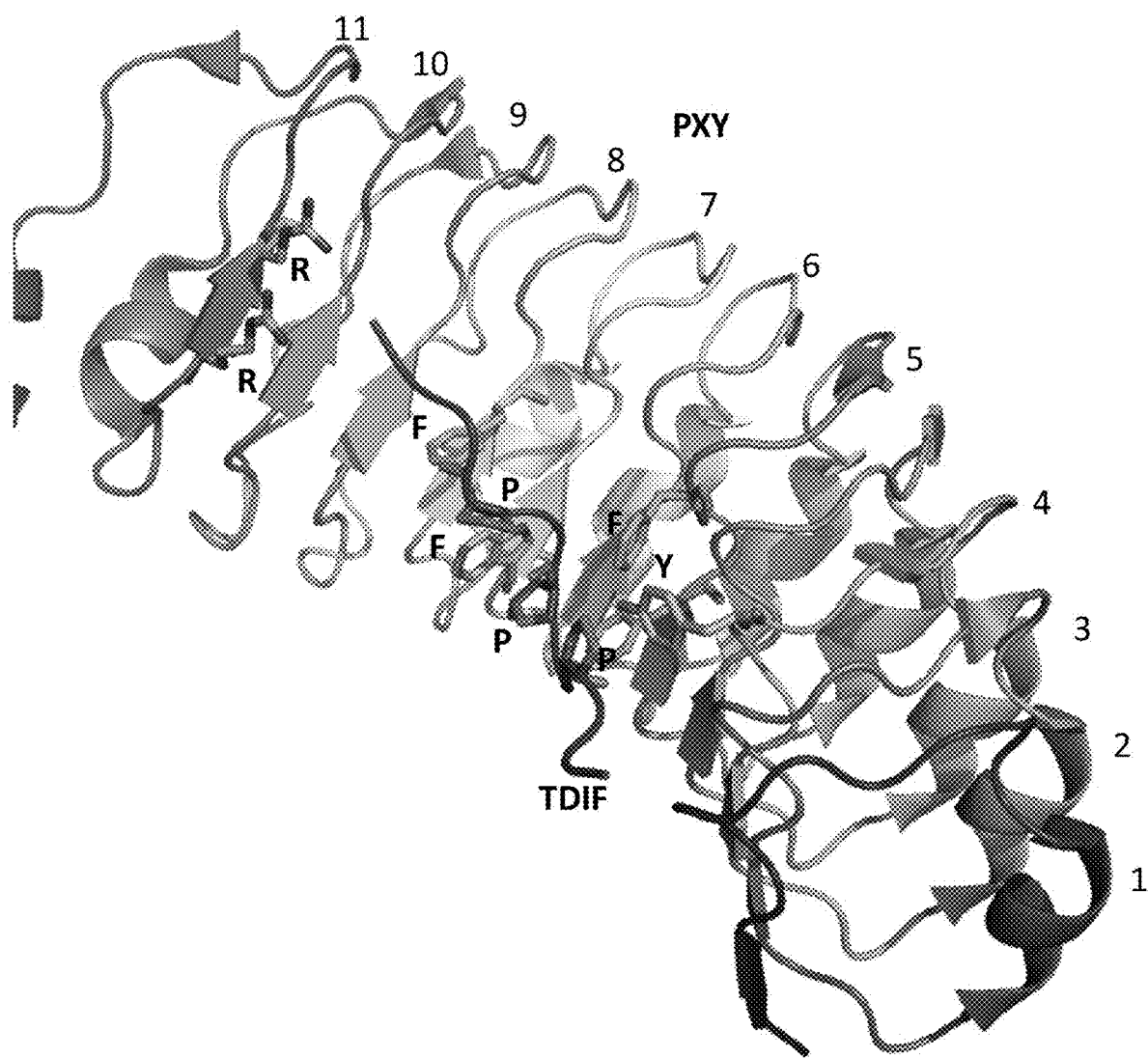

FIG. 5 shows modeling of a structurally similar receptor-ligand interaction of PXY receptor and TDIF ligand.

The sequence descriptions (Table 1) and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (2):345-373 (1984) which are herein incorporated by reference. The symbols and format used for nucleotide and amino acid sequence data comply with the rules set forth in 37 C.F.R. § 1.822.

TABLE 1

Sequence description

| SEQ ID NOS | Description |
|---|---|
| 1 | fea3-TS1 |
| 2 | fea3-TS2 |
| 3 | fea3-TS3 |
| 4 | Cas9 cassette |
| 5 | SV40-NLS |
| 6 | U6 POLIII PRO |
| 7 | fea3-CR1 |
| 8 | fea3-CR2 |
| 9 | fea3-CR3 |
| 10 | fea3-TS3-oligo-1 |
| 11 | fea3-TS3-oligo-2 |
| 12 | fea3-TS3-oligo-3 |
| 13 | fea3-TS2-oligo-1 |
| 14 | fea3-TS2-oligo-2 |
| 15 | fea3-f1 |
| 16 | fea3-r1 |
| 17 | Universal F primer |
| 18 | 2nd NGS index pair |
| 19 | fea3-genomic seq |
| 20 | guide RNA |
| 21 | Zm fea3 wild-type (amino acid) |
| 22 | Zm fea3 shorter spliced sequence (amino acid) |
| 23 | Zm fea3 wild-type (506 amino acids) |
| 24 | Zm fea3 wild-type (478 amino acids) |
| 25 | Zm fea3 promoter |
| 26 | Zm fea3 3'-UTR |
| 27 | Rice homolog (amino acid) |
| 28 | EMS fea3-2 mutant nucleotide sequence |
| 29 | Repair template 1 (Fea3-TS3) |
| 30 | Repair template 2 (Fea3-TS3) |
| 31 | Repair template 3 (Fea3-TS3) |
| 32 | Repair template 1 (Fea3-TS2) |
| 33 | Repair template 2 (Fea3-TS2) |
| 34 | ZmFCP1 amino acid (mature) |
| 35 | Rep1 LRR |
| 36 | Rep2 LRR |
| 37 | Rep3 LRR |
| 38 | Rep4 LRR |
| 39 | Rep5 LRR |
| 40 | Rep6 LRR |
| 41 | Rep7 LRR |
| 42 | Rep8 LRR |
| 43 | Rep9 LRR |
| 44 | Rep10 LRR |
| 45 | Rep11 LRR |
| 46 | Rep12 LRR |

The sequence description and Sequence Listing attached hereto comply with the rules governing nucleotide and/or amino acid sequence disclosures in patent applications as set forth in 37 C.F.R. § 1.821-1.825.

The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984) which are herein incorporated by reference. The symbols and format used for nucleotide and amino acid sequence data comply with the rules set forth in 37 C.F.R. § 1.822.

DETAILED DESCRIPTION OF THE DISCLOSURE

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Modified" refers to any cell, cell line, callus, tissue, plant part or plant, the genome of which has been altered by the presence of a heterologous nucleic acid, such as a recombinant DNA construct, including those initial modified events as well as those created by sexual crosses or asexual propagation from the initial modified event. The term "modified" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Agronomic characteristic" is a measurable parameter including but not limited to, ear meristem size, tassel size, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root branching, root biomass, root lodging, harvest index, stalk lodging, plant height, ear height, ear length, salt tolerance, early seedling vigor and seedling emergence under low temperature stress.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to a polynucleotide sequence that when transcribed, processed, and/or translated results in the production of a polypeptide sequence.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

The phrase "interaction of the FEA3 polypeptide with a ligand is modulated" generally refers to a change in the interaction of the FEA3 polypeptide with its ligand, when compared to the wild-type FEA3 polypeptide's interaction with its natural unmodified ligand. This change in the interaction can result in a stronger or a weaker interaction as compared to the wild-type control, where the FEA3 polypeptide or its ligand are unmodified.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in modified organisms that exceeds levels of production in a null segregating (or non-modified) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or modified to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches. Silencing may be targeted to coding regions or non-coding regions, e.g., introns, 5'-UTRs and 3'-UTRs, or both.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

The term "locus" generally refers to a genetically defined region of a chromosome carrying a gene or, possibly, two or more genes so closely linked that genetically they behave as a single locus responsible for a phenotype. When used herein with respect to Fea3, the "Fea3 locus" or "fea3 genomic locus" shall refer to the defined region of the chromosome carrying the Fea3 gene including its associated regulatory sequences.

A "gene" shall refer to a specific genetic coding region within a locus, including its associated regulatory sequences. One of ordinary skill in the art would understand that the associated regulatory sequences will be within a distance of about 2-10 kb from the Fea3 coding sequence, with the promoter located upstream.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, WI). Unless stated otherwise, multiple alignment of the sequences provided herein were performed using the Clustal W method of alignment.

The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB.

After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner.

The present disclosure includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NOS: 20-21, 25; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs to design and target the fea3 genomic locus of the present disclosure. The polypeptide is preferably a FEA3 polypeptide. The polypeptide preferably has a spectrum of FEA3 activity.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NOS: 19, 26; a nucleic acid sequence listed in Table 1 or (ii) a full complement of the nucleic acid sequence of (i). Any of the foregoing isolated polynucleotides may be utilized in any recombinant DNA constructs (including suppression DNA constructs) of the present disclosure. An isolated polynucleotide comprising a nucleotide sequence, wherein the nucleotide sequence is hybridizable under stringent conditions with a DNA molecule comprising the full complement of a nucleotide sequence listed in Table including SEQ ID NOS:19, 26.

An isolated polynucleotide comprising a nucleotide sequence, wherein the nucleotide sequence is derived from SEQ ID NO:19 or 26 by alteration of one or more nucleotides by at least one method selected from the group consisting of: deletion, substitution, addition and insertion.

An isolated polynucleotide comprising a nucleotide sequence, wherein the nucleotide sequence corresponds to an allele of SEQ ID NO: 19 or 26.

In one embodiment, the present disclosure includes recombinant DNA constructs (including suppression DNA constructs). The recombinant DNA construct (including suppression DNA constructs) may comprise a polynucleotide of the present disclosure operably linked, in sense or antisense orientation, to at least one regulatory sequence (e.g., a promoter functional in a plant). The polynucleotide may comprise 100, 200, 300, 400, 500, 600, 700, 800, 900 or 1000 contiguous nucleotides of SEQ ID NO:1, 2, 4, 18, 20, 22, 24 or 26. The polynucleotide may encode a polypeptide of the present disclosure.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

It is well understood by those skilled in the art that different promoters may direct the expression of a gene in different tissues or cell types, or at different stages of development, or in response to different environmental conditions.

A wild-type maize FEA3 or "fasciated ear3" gene encodes a predicted leucine rich repeat receptor-like protein (LRR-RLP) of 506 amino acids. The terms "wild-type FEA3 gene", "FEA3 wt gene", "Fea3 gene" and "FEA3 gene" are used interchangeably herein. *Arabidopsis* contains three FEA3 orthologues At3g25670, At1g 13230, and At1g68780. The term fasciation, from the Latin fascis, meaning bundle, describes variations in plant form resulting from proliferative growth.

Plants with fea3 mutations, wherein the mutation results in a loss of FEA3 function or loss of FEA3 expression are also called "fea3 plants" or "fea3 null plants". "fea3 null plants" exhibit the "fea3 phenotype" or the "fea3 null phenotype". fea3 plants develop larger meristems during inflorescence and floral shoot development, and ear inflorescence meristems show severe fasciation, suggesting that fea3 normally acts to limit the growth of these meristems.

Plants with weak fea3 mutations, wherein the mutation results in a partial loss of fea3 function or partial loss of fea3 expression are also called "fea3 plants with weak fea3 phenotype". "weak fea3 plants" exhibit the "weak fea3 phenotype". fea3 plants with weak fea3 alleles exhibit similar phenotype as the fea3 null plants, but to a lesser extent. fea3 plants with weak fea3 alleles may also exhibit partial fea3 null phenotype, that is may not exhibit all the fea3 null characteristics. "Weak fea3 alleles" as referred to herein are fea3 variants or variants of SEQ ID NOS: 21, 22, 23, 24, which confer weak fea3 phenotype on the plant.

Plants with fea3 mutations that exhibit "null fea3 phenotype" or "weak fea3 phenotype" are referred to herein as plants with "mutant fea3 phenotype".

The term "dominant negative mutation" as used herein refers to a mutation that has an altered gene product that acts antagonistically to the wild-type allele. These mutations usually result in an altered molecular function (often inactive) and are characterized by a "dominant negative" phenotype. A gene variant, a mutated gene or an allele that confers "dominant negative phenotype" would confer a "null" or a "mutated" phenotype on the host cell even in the presence of a wild-type allele.

As used herein, a polypeptide (or polynucleotide) with "FEA3 activity" refers to a polypeptide (or polynucleotide), that when expressed exhibits the "fea3 mutant phenotype", and is capable of partially or fully rescuing the fea3 mutant phenotype.

The terms "gene shuffling" and "directed evolution" are used interchangeably herein. The method of "gene shuffling" consists of iterations of DNA shuffling followed by appropriate screening and/or selection to generate variants of FEA3 nucleic acids or portions thereof having a modified biological activity (Castle et al., (2004) Science 304(5674): 1151-4; U.S. Pat. Nos. 5,811,238 and 6,395,547).

The term "yield related agronomic characteristic" generally refers to a parameter that serves as a measure for yield, for example, kernel number, kernel rows, kernel weight, ear length, ear width, kernel size, and a combination of the foregoing.

I. Gene Editing

In some embodiments, gene editing may be facilitated through the induction of a double-stranded break (DSB) or single strand break (e.g., nicking) in a defined position in the genome near the desired alteration for example fea3 genomic locus. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 *Nature Methods Vol.* 10: 957-963.) The polynucleotide modification template may be present transiently in the cell or it can be introduced via a viral replicon.

A "modified nucleotide" or "edited nucleotide" refers to a nucleotide sequence of interest (e.g., fea3) that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i) (iii).

The term "polynucleotide modification template" includes a polynucleotide that comprises at least one nucleotide modification when compared to the nucleotide sequence to be edited (e.g., fea3). A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) *Nature Biotechnology* 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) *FASEB* 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, *Science* 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

Any guided endonuclease can be used in the methods disclosed herein. Such endonucleases include but are not limited to Cas9 and Cpf1 endonucleases. Many endonucleases have been described to date that can recognize specific PAM sequences (see for example—Jinek et al. (2012) Science 337 p 816-821, PCT patent applications PCT/US16/32073, filed May 12, 2016 and PCT/US16/32028 filed May 12, 2016 and Zetsche B et al. 2015. Cell 163, 1013) and cleave the target DNA at a specific position. It is understood that based on the methods and embodiments described herein utilizing a guided Cas system one can now tailor these methods such that they can utilize any guided endonuclease system.

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015, both are hereby incorporated in its entirety by reference.)

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to direct a guide polynucleotide/Cas endonuclease complex to a unique DNA target site.

The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

In addition to modification of Fea3 locus by a double strand break technology, modification of one or more bases without such double strand break are achieved using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533 (7603):420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous Fea3 locus to create target variations and improve grain yield. Similarly, adenine base editors enable adenine to inosine change, which is then converted to guanine through repair or replication. Thus, targeted base changes i.e., C•G to T•A conversion and A•T to G•C conversion at one or more locations of the Fea3 genomic locus or the genomic locus encoding a corresponding ligand, e.g., ZmFCP1 polypeptide are made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR—Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, CA, 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

The plant containing the mutated fea3 gene can be crossed with other plants to introduce the mutation into another plant. This can be done using standard breeding techniques.

Homologous recombination allows introduction in a genome of a selected nucleic acid at a defined selected position. Homologous recombination has been demonstrated in plants. See, e.g., Puchta et al. (1994), *Experientia* 50: 277-284; Swoboda et al. (1994), *EMBO J.* 13: 484-489; Offringa et al. (1993), *Proc. Natl. Acad. Sci. USA* 90: 7346-7350; Kempin et al. (1997) *Nature* 389:802-803; and, Terada et al., (2002) *Nature Biotechnology*, 20(10): 1030-1034).

EMBODIMENTS

In one embodiment, the fea3 variant that can be used in the methods of the current disclosure is one or more of the following fea3 nucleic acid variants: (i) a portion of a fea3 nucleic acid sequence (SEQ ID NO: 19); (ii) a nucleic acid sequence capable of hybridizing with a fea3 nucleic acid sequence (SEQ ID NO:19); (iii) a splice variant of a fea3 nucleic acid sequence; (iv) a naturally occurring allelic variant of a fea3 nucleic acid sequence; (v) a fea3 nucleic acid sequence obtained by gene shuffling or site-specific genome editing; (vi) a fea3 nucleic acid sequence obtained by site-directed mutagenesis; (vii) a fea3 variant obtained and identified by the method of TILLING.

In one embodiment, the levels of endogenous FEA3 expression can be decreased in a plant cell by genomic disruptions. Examples of genomic disruption include, but are not limited to, disruptions induced by CRISPR-Cas endonucleases, transposons, tilling, homologous recombination.

In one embodiment, a nucleic acid variant of FEA3 useful in the methods of the disclosure is a nucleic acid variant obtained by gene shuffling and having those gene shuffled variations introduced by genome editing techniques described herein.

In one embodiment, a genetic modification may also be introduced in the locus of a maize FEA3 gene using the technique of CRISPR-Cas endonucleases.

In one embodiment, site-directed mutagenesis may be used to generate variants of fea3 nucleic acids.

In one embodiment homologous recombination can also be used to modulate, inactivate, or reduce the expression of endogenous FEA3 gene in a plant.

Homologous recombination can be used to induce targeted gene modifications by specifically targeting the FEA3 gene in vivo. Mutations in selected portions of the FEA3 gene sequence (including 5' upstream, 3' downstream, and intragenic regions) such as those provided herein are made in vitro and introduced into the desired plant using standard techniques. Homologous recombination between the introduced mutated fea3 gene and the target endogenous FEA3 gene would lead to targeted replacement of the wild-type gene in modified plants, resulting in suppression of FEA3 expression or activity.

In one embodiment, the genomic modification step comprises producing one or more mutations in the FEA3 gene sequence, where the one or more mutations in the FEA3 gene sequence comprise one or more insertions, thereby modifying the FEA3 gene compared to a corresponding control plant. For example, the mutation may comprise a homozygous disruption in the FEA3 gene or the one or more mutations comprise a heterozygous disruption in the FEA3 gene.

EXAMPLES

The present disclosure is further illustrated in the following Examples, in which parts and percentages are by weight and degrees are Celsius, unless otherwise stated. It should be understood that these examples, while indicating embodiments of the disclosure, are given by way of illustration only.

From the above discussion and these Examples, one skilled in the art can ascertain the essential characteristics of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Fea3 Genome Editing

Target Site Selection

The gRNA/Cas9 site directed nuclease system, described in WO2015026885, WO20158026887, WO2015026883, and WO2015026886, was used to edit the fea3 gene in maize (U.S. Pat. No. 9,701,979B2), which is incorporated by reference herein). To edit the fea3 gene at its endogenous allele with an amino acid substitution at 417 from Cysteine to Tyrosine, to recapitulate the fea3-2 mutant, or to create fea3-2 like weaker alleles, the following target sites were used: fea3-TS1, fea3-TS2, and fea3-TS3 (SEQ ID NOS: 1-3). The location of each target site in the fea3 genomic sequence (SEQ ID NO:19) is shown in FIG. 1 (a), and target sequences are listed in Table 2.

TABLE 2 fea3 Target Site Sequences

| Target Site Designation | Maize Genomic Target Site Sequence | PAM Sequence |
|---|---|---|
| Fea3-TS1 | SEQ ID NO: 1 | CGG |
| Fea3-TS2 | SEQ ID NO: 2 | CGG |
| Fea3-TS3 | SEQ ID NO: 3 | GGG |

Cas9 Vector Construction

The Cas9 gene from *Streptococcus pyogenes* M1 GAS (SF370) and the potato ST-LS1 intron was introduced in order to eliminate its expression in *E. coli* and *Agrobacterium*. To facilitate nuclear localization of the Cas9 protein in maize cells, the Simian virus 40 (SV40) monopartite amino terminal nuclear localization signal (SEQ ID NO:5) was incorporated at the amino terminus of the Cas9 open reading frame. The Cas9 gene was operably linked to a maize Ubiquitin promoter using standard molecular biological techniques. SEQ ID NO: 4 represents the Cas9 cassette.

Guide RNA Vector Construction

To direct the Cas9 nuclease to the designated genomic target sites, a maize U6 polymerase III promoter (SEQ ID NO:6; see WO2015026885, WO20158026887, WO2015026883, and WO2015026886) and its cognate U6 polymerase III termination sequences were used to direct initiation and termination of gRNA expression. The guide RNA coding sequence was 77 bp long (SEQ ID NO:20) and comprised a 12-30 bp variable targeting domain chosen from a maize genomic target site. Guide RNA variable targeting domains for fea3 gene editing are identified as fea3-CR1, fea3-CR2, and fea3-CR3 which correspond to the genomic target sites fea3-TS1, fea3-TS2, and fea3-TS3, respectively. DNA encoding each of the variable nucleotide targeting domains was cloned into a gRNA expression cassette through BsbI sites using double strand oligos.

TABLE 3 fea3 Guide RNA variable targeting domains

| Name | DNA version of guide RNA |
|---|---|
| fea3-CR1 | SEQ ID NO: 7 |
| fea3-CR2 | SEQ ID NO: 8 |
| fea3-CR3 | SEQ ID NO: 9 |

Oligo Repair Template

Oligos of the substitution/repair template for fea3-TS2 and fea3-TS3 contained the nuclear tide substitution for C417Y from G to A and the homology sequences flanking the fea3-TS2 or fea3-TS3. The alignment of fea3-TS3 and fea3-TS2 with the corresponding oligo repair templates are shown in FIG. 2 in a schematic illustration. The complete sequences of oligo templates are listed in Table 4. Sense and anti-sense strand of oligos were synthesized, annealed together to form double strand oligos (dsOligo) according to standard annealing process.

TABLE 4 fea3 oligo repair template

| Target Site | Oligo Name | SEQ ID NO: |
|---|---|---|
| Fea3-TS3 | fea3-TS3-oligo-1 | 10 |
| Fea3-TS3 | fea3-TS3-oligo-2 | 11 |
| Fea3-TS3 | fea3-TS3-oligo-3 | 12 |
| fea3-TS2 | fea3-TS2-oligo-1 | 13 |
| fea3-TS2 | fea3-TS2-oligo-2 | 14 |

Delivery of the Guide RNA/Cas9 Endonuclease System DNA to Maize

Plasmids containing the Cas9 and guide RNA expression cassettes and repair oligo template described above were co-bombarded with plasmids containing the transformation selectable marker NPTII and the transformation enhancing developmental genes ODP2 (AP2 domain transcription factor ODP2 (Ovule development protein 2)) and Wuschel into elite maize lines' genomes. Transformation of maize immature embryos can be performed using any method known in the art or the method described below.

In one transformation method, ears are husked and surface sterilized in 30-50% Clorox bleach plus 0.5% Micro detergent for 10 minutes and then rinsed two times with sterile water. The immature embryos are isolated and placed embryo axis side down (scutellum side up), with 25 embryos per plate, on 13224E medium for 2-4 hours and then aligned within the 2.5-cm target zone in preparation for bombardment.

DNA of plasmids and oligo is adhered to gold pellets using a lipid-polymer mixture. A DNA solution was prepared using 1 µg of plasmid DNA and optionally, other constructs were prepared for co-bombardment using 10 ng (0.5 µl) of each plasmid. The sample plates are bombarded with a Biolistic PDA-1000/He (Bio-Rad). Embryos are 6 cm from the macrocarrier, with a gap of ⅛th of an inch between the 200 psi rupture disc and the macrocarrier. All samples received a single shot. Following bombardment, the embryos are incubated on the bombardment plate and then transferred rest/induction medium. Embryos are then transferred to the maturation media. Mature somatic embryos are then transferred to germination media and moved to the light. In about 1 to 2 weeks, plantlets containing viable shoots and roots are sampled for analysis and sent to the greenhouse where they are transferred to flats (equivalent to a 2.5" pot) containing potting soil. After 1-2 weeks, the plants are transferred to Classic 600 pots (1.6 gallon) and grown to maturity.

Screening of T0 Plants and Variants (Events)t Characterization

To identify fea3 edited variants, genomic DNA was extracted from leaf tissue of T0 plants. Next Generation Sequencing (NGS) (Illumina) was used to identify the edited T0 variants. The region was PCR amplified with PHUSION® Flash High Fidelity PCR Master Mix (Termo Scientific, F-531). The primers used in the primary PCR reaction are shown in Table 5 and indicated in FIG. 1 (a) for their positon to fea3-TS3. The primers used in the secondary PCR reaction are provided in SEQ ID NO:17 and SEQ ID NO:18, "NNNNNNNN" in the reverse primer is the barcode sequence corresponding to a sample location on a plate.

TABLE 5

Primers Used to Screen edited variants

| Target | Primer name | Primer Orientation | Primer SEQ ID NO: |
|---|---|---|---|
| Fea3-TS3 | fea3-f1 | Forward | SEQ ID NO: 15 |
| Fea3-TS3 | fea3-r1 | Reverse | SEQ ID NO: 16 |

A summary of the T0 edits is shown in Table 6. Fea3-2 edited variants were obtained in both stiff stalk and non-still stalk lines transformed. Additional SNPs in the oligo template of fea3-TS3-oligo2 showed higher edit efficiency.

TABLE 6

Summary of fea3-2 edit Events

| dsOligo template | genotype | #embryo used | # T0 plant | #T0 w/edit (qPCR) | #T0 w/edit (NGS) |
|---|---|---|---|---|---|
| 1 | A | 750 | 144 | 12 | 6 |
|   | B | 1510 | 62 | 3 | 1 |
| 2 | A | 714 | 162 | 24 | 16 |
|   | B | 2057 | 55 | 8 | 2 |

T1 Analysis

The fea3 edited T0 plants were transferred to a controlled environment. T0 plants were back crossed with recurrent parent plants to produce T1 (BC0) seeds. T1 (BC0) plants went through more comprehensive molecular characterization to not only confirm that edits observed in T0 plant were stably inherited but also to verify that the T1(BC0) or later generation plants were free from any foreign DNA elements used during the transformation process.

Same assays for identifying edit variants used at T0 stage were performed on T1 (BC0) plant samples to confirm edit present. qPCR was performed on all helper genes including Cas9, the guide RNAs, the transformation selection marker (NPTII), and the transformation enhancing genes ODP2 and WUS2 to confirm that the genes segregated away from the generated edit alleles. Selected T1(BC0) plants (plants with edit and null segregants) is analyzed with Southern by Sequencing (SbS) to further support that the plants are free of any foreign DNA. Homozygous edited plants from male and female will be crossed to make hybrid for further phenotyping and yield evaluation.

Example 2

Fea3 Variant Generation Through Genome Editing

Example 1 provides several methods to generate fea3 variants in vivo. fea3 sequences such as promoter region, UTR, genomic sequences, splice variant sequence and other regulatory regions are disclosed herein. Phenotype of fea3-2 allele and its impact on kernel number is provided. Based on the guidance provided herein and the functional aspect of fea3 in the organ primordia development, one or more of the following approaches are undertaken by targeted genomic modification of the fea3 locus:

Reduced expression of a polynucleotide encoding the fea3 polypeptide is achieved by mutating one or more of regulatory element in the fea3 genomic locus. Reduced activity of the fea3 polypeptide, such as for example, reduced ability to bind signaling peptides or molecules from the meristem developmental pathway, is modulated by modifying one or more amino acid residues in the receptor domain of fea3. In addition, generation of one or more alternative spliced transcripts of a polynucleotide encoding the fea3 polypeptide is also performed by engineering a splice junction into the fea3 genomic locus such that a shorter transcript is produced. Deletion of one or more domains of the fea3 polypeptide may also result in reduced fea3 activity. Introducing frameshift mutation in one or more exons of a polynucleotide encoding the fea3 polypeptide can result in weaker alleles of the fea3 mutant. Deletion of a substantial portion of the polynucleotide encoding the fea3 polypeptide or deletion of the polynucleotide encoding the fea3 polypeptide is also possible through genome editing approaches. Repression of an enhancer motif present within a regulatory region encoding the fea3 polypeptide can also result in reduced gene expression. Modification of one or more nucleotides or deletion of a regulatory element (e.g., promoter or UTR) operably linked to the expression of the polynucleotide encoding the fea3 polypeptide, wherein the regulatory element is present within a promoter, intron, 3'UTR, terminator or a combination thereof. A mutation in or near the Leucine Rich Repeat (LRR) domain of fea3 polypeptide or a) mutation in or near the domain of fea3 exposed to extracellular signaling factors involved in the development of organ primordia can also modulate fea3 expression or activity.

Example 3

Phenotypic Characteristics of Fea3 Genome Edited Plants

Genome edited maize plants that correspond to the fea3-2 mutation (as shown in FIGS. 1-2) were obtained as described herein. Hand-pollinated F3 ears from homozygous fea3-2 edited (HO) and null-segregant variant null (VN) sibling plants were harvested at maturity after propagation under greenhouse conditions (FIG. 3). Five ear images from HO and VN were analyzed by ear photometry analysis, e.g., as described in U.S. Pat. No. 8,073,235B2, incorporated by reference herein for computing kernels per ear (KPE). Average and minimum and maximum range in KPE (error bars) are plotted in the bar graph (FIG. 3, left panel), and representative HO and VN ear images are shown side-by-side (FIG. 3, right panel). The analysis was repeated, and kernel number was tabulated as shown on the graph of FIG.

3. As shown, genome edited plants exhibited about ~12% gain in kernel numbers based on a representative inbred ear analysis.

This example demonstrates that genome edited plants where a modification to the fea3 locus was achieved using site-specific DNA modification technique resulted in an increase of kernel numbers per year, indicating a positive observation of a yield trait. Similar ear photometry analysis is performed for other modifications of the fea3 locus.

Maize inbred line 1 and line 2 were genome edited via CRISPR-Cas9 facilitated Homology directed repair (HDR), substituted the amino acid Cysteine at 417 with Tyrosine separately. Increased kernel number on ears from Homozygous CRISPR fea3-2 compared to variant null at BC1F3 generation was observed. Results are summarized for inbred line 2 in Table 7.

TABLE 7

Kernel number analysis of inbred line 2

| Ear No. | Fea3-2 (homozygous) - Inbred line 2 - kernels/ear | Null Variant (control) - kernels/ear |
| --- | --- | --- |
| 1 | 253 | 273 |
| 2 | 249 | 223 |
| 3 | 282 | 184 |
| 4 | 297 | 230 |
| Avg: | 270 | 227 |

The hybrid from crossing of the female and male CRISPR fea3-2 are evaluated. One row of fea3 edit and one row of null variants were evaluated in a limited field trial and ear photometry was performed. 10 ears from the fea3 edited row and 10 ears from the null variant row were evaluated. Grain yield per acre was increased in the fea3 row compared to the null control row, number kernel rows in fea3 was slightly decreased compared to the null control, kernels per row was increased in fea3 edited material compared to the null control, total number of kernels per ear was increased in the fea3 edited material compared to the null control, total length of harvested cob was increased in fea3 compared to control, ear width was slightly reduced in fea3 edited material, estimated ear volume and ear area were increased in fea3 edited ear compared to the null control, and percent of ear length affected by kernel abortion was reduced in fea3 edited ear compared to the null control. However, based on the limited data points available from the two-row trial, statistical significance was not observed for these phenotypic characteristics. Multi-row, multi-location and/or with additional backgrounds can help evaluate these phenotypic characteristics to a greater resolution and with statistical significance.

Example 4

Identification of Target Sites for Modification in Fea3

Modeling and sequence mapping work was performed for ZmFea3 on the basis of PXY-CLE41-SERK2 and other LRR-peptide-LRR complexes. AtFLS2-flg22-BAK1, a plant defense signaling complex may be similar to fea3 signaling in plants. In this system, pathogenic peptide (flg22) binds to FLS2's LRR domain. Flg22 further induces a heterodimerization of FLS2 with BAK1, another LRR containing protein to initialize signaling process. Both proteins (FLS2 and fea3) have a conserved disulfide bond securing N-terminal CAP, indicating a possibility to modulate the fea3 structure stability by mutating the corresponding cysteines like C435Y mutant. One approach to modulate Fea3 function is by changing the protein-peptide interface residues. Although the repeat units in Fea3 sequence are divergent substantially, with a careful inspection, the canonical motif (LxxLxLXX[N/C]xL) among all the 12 LRR repeats, was identified and were aligned (FIG. 4). Each LRR repeat includes generally of about 24 amino acid residues and form a ring or disk structure with β-strand-loop-α-helix topology (FIG. 4B). Multiple repeats stack their disk/rings together to form a horseshoe structure with their β-strand sides in the concave face, suitable for peptide or protein binding (FIG. 4). The highly conserved Ls and N/C are internal/core facing and provide the major core packing materials while the variant residues at x positions are exposed to the concave face, ready to ligand recognition (FIG. 4). The TDIF peptide is similar to ZmFCP1, especially conserved at three Prolines. TDIF binds to the concave groove serving molecular glue to recruit SERKs (FIG. 5). Recognition residues in PXY are the aromatic amino acids stacking with TDIF proline rings. The two positively charged Rs are also identified by interacting with TDIF's C-terminus For genome editing purposes, in certain embodiments, disrupting one or more conserved Leucine residues may substantially impact the structural integrity of the Fea3 protein. However, the concave facing residues at x positions (identified in FIG. 4A) are tolerant for amino acid changes, and targeted mutations of these residues can modulate ligand binding affinity and/or specificity. Based on the PXY-CLE41-SERK2 model, a suitable list of aromatic and positively charged residues as mutation candidates is disclosed here. The numbers correspond to the amino acid positions present in Fea3 protein as noted by SEQ ID NO: 23—R127, R128, R130, F134, R164, R208, R209, R242, Y244, K261, R357, F358, H363, Y384. In some embodiments, these residues are changed to neutral amino acid residues such as alanine or glycine. Conservative substitutions can be made for example, for Ala (V, L, I), for Arg (K, Q, N), for Asn Q, H, K, R), for Asp (E), Cys (S), for Gln (N), for Glu (D), for His (N, Q, K, R), for Ile (L, V, M, A, F), for Leu (I, V, M, A, F), for Lys (R, Q, N), for Met (L, F, I), for Phe (L, V, I, A) and Pro (G).

Example 5

Modulation of FEA3 Ligand ZmFCP1 Binding and Activity

FON2-LIKE CLE PROTEIN1 (FCP1), for example in rice, is expressed predominantly in the shoot apical meristem, floral meristem and root apical meristem. The maize ortholog is designated ZmFCP1. ZmFCP1 peptide (REVPTGPDPIHH—SEQ ID NO: 34) signals through FEA3 to restrict stem cell proliferation using a signal expressed in differentiating cells in organ primordia. As described previously, FEA3 encodes an LRR-receptor-like protein, with a predicted signal peptide followed by 12 leucine rich repeats (LRRs), a transmembrane domain, and a cytoplasmic tail.

Any of the residues in the mature ZmFCP1 twelve amino acid peptide ligand can be edited in the corresponding genomic sequence of the ZmFcp1 genomic locus as an approach to modulate ZmFCP1-Fea3 interaction. In addition, nucleotide modifications can also be introduced at the genomic locus encoding the ZmFCP1 Pre-Pro-Peptide (94 amino acids) encoded by the ZmFcp1 gene. Amino acid variations to ligand domain preserve the genomic structure and regulatory elements (such as promoter sequences) controlling spatial and temporal expression of ZmFcp1, enabling production of modified ligands in the appropriate tissues and within the appropriate developmental timing typical of ZmFCP1. Such site-specific edits altering the mature ligand may affect processing or otherwise modify or weaken the ligand/receptor/interactor binding(s), such as to Fea3 and/or its interacting partners. Based on an alignment of known CLE-like peptides, ligand modifications (from N-terminal to C-terminal of SEQ ID NO: 34 include:

a. E to I, E to T, E to R, E to L, E to M, E to K, E to A, E to S,
b. V to S, V to I, V to A,
c. T to S, T to N, T to G, T to E, T to Q, T to R, T to A
d. G to C, G to S,
e. P to A, P to S,
f. D to N,
g. P to H,
h. I to L, I to K, I to Q, I to M,
i. HH to HN,

These variations can be assayed in growth chamber or green house conditions and using ear photometry solutions to observe differences in ear parameters such as kernel numbers.

What is claimed is:

1. A method of producing a modified maize plant with an increase in kernel number, the method comprising:
   a. introducing one or more site-specific nucleotide mutations at an endogenous fea3 locus within the maize genome, wherein the endogenous fea3 locus encodes a FEA3 polypeptide comprising an amino acid sequence that is at least 95% identical to SEQ ID NO: 23;
   b. generating a population of modified maize plants comprising the one or more site-specific mutations at the endogenous fea3 locus; and
   c. selecting the modified plant of (b), wherein the modified maize plant exhibits an increase in kernel number, when compared to a control maize plant not comprising the one or more mutations,
   wherein the one or more site-specific mutations are introduced at the fea3 genomic locus such that one or more amino acid positions selected from the group consisting of C79, C89, R127, R128, R130, F134, R164, R208, R209, R242, Y244, K261, R357, F358, H363, Y384, and C417 of SEQ ID NO: 23 are mutated.

2. The method of claim 1, where in the site-specific nucleotide changes are introduced by a RNA-guided Cas endonuclease.

3. The method of claim 1, wherein the site-specific nucleotide changes are introduced by a base editor in the absence of a double strand break.

4. The method of claim 1, wherein the site-specific nucleotide changes are introduced at the genomic locus such that the interaction of the FEA3 polypeptide with a ligand is modulated.

5. The method of claim 4, wherein the ligand is ZmFCP1.

6. The method of claim 1, wherein the one or more site-specific nucleotide mutations are introduced at the endogenous fea3 locus of SEQ ID NO:23 within the maize genome such that the activity and/or expression of the locus is reduced.

* * * * *

```
                       SEQUENCE LISTING

<160> NUMBER OF SEQ ID NOS: 46

<210> SEQ ID NO 1
<211> LENGTH: 22
<212> TYPE: DNA
<213> ORGANISM: Zea mays

<400> SEQUENCE: 1
gggctgtgct acaacgtcgc gg                                             22

<210> SEQ ID NO 2
<211> LENGTH: 22
<212> TYPE: DNA
<213> ORGANISM: Zea mays

<400> SEQUENCE: 2
gcgacgttgt agcacagccc gg                                             22

<210> SEQ ID NO 3
<211> LENGTH: 21
<212> TYPE: DNA
<213> ORGANISM: Zea mays

<400> SEQUENCE: 3
gcgtcgtggg acaaccccgg g                                              21

<210> SEQ ID NO 4
<211> LENGTH: 4107
<212> TYPE: DNA
<213> ORGANISM: Artificial Sequence
<220> FEATURE:
<223> OTHER INFORMATION: Vector

<400> SEQUENCE: 4
atggataaga agtacagcat cggcctcgac atcgggacca acagcgtcgg ctgggccgtc    60
atcaccgacg aatataaggt gcccagcaag aagttcaagg tgctcgggaa tacagaccgc   120
cacagcatca agaagaacct gatcggcgcc ctcctgttcg actcgggcga gaccgctgag   180
gccaccagac taaagaggac cgctcgccgc cgctacaccc gccgcaagaa ccgcatatgc   240
tacctccagg agatcttcag caacgagatg gccaaggtgg acgacagctt cttccaccgc   300
cttgaggagt cgttcctcgt ggaggaggac aagaagcatg agaggcaccc gatcttcggg   360
aacatcgtgg acgaggtggc gtaccacgag aagtacccga cgatctacca cctccgcaag   420
aagctggtcg actccacaga caaggccgac ctcagactga tctacctggc cctcgcgcac   480
atgatcaagt tccgcgggca cttcctcatc gagggcgacc tgaacccgga caactccgac   540
gtcgacaagc tcttcatcca gctggtccag acctacaatc aactgttcga ggagaacccg   600
```

```
atcaacgcgt ccggcgtgga cgcgaaggcc atcctcagcg cgaggctcag caaatcaaga    660
cggctggaga acctgatcgc ccagctccca ggcgagaaga aaaacggctt gttcggcaac    720
ctgatcgcgc tctcgctcgg cctcacgccc aacttcaaat caaacttcga cctggccgag    780
gacgcgaaac tgcagctgtc caaggacact tacgacgacg acctcgacaa cctgctggcg    840
caaatcggtg accagtacgc agacctcttc ctggccgcca agaacctctc ggacgccatc    900
ctgctgtccg atatcctgag agtgaatacg agatcacca aggcgccgct cagcgcctcc    960
atgattaaaa ggtacgacga gcaccaccag gacctgacgc tgctcaaggc cctggtgcgc   1020
cagcagctcc ccgagaagta caaggagatc ttcttcgacc aatcaaaaaa cggctacgcc   1080
ggctacatcg acggggcgc ctcccaggag gagttctaca agttcatcaa accaattctc   1140
gagaagatgg acgcacgga ggagcttctc gtgaagctca accgggagga cctcctgagg   1200
aagcagagga cgttcgacaa cggctcgata ccgcatcaga tccacctggg cgagctccac   1260
gccatcctgc gccggcagga ggatttctat ccgttcctca aggacaacag ggagaagatc   1320
gagaaaattc tgacgttccg catcccgtac tacgtgggcc ctctcgcgcg cgggaacagc   1380
cggttcgcct ggatgactcg gaagtcggag gagacgatca cgccgtggaa cttcgaggag   1440
gtggtggaca agggcgcctc cgcccagtcg ttcatcgagc gcatgacgaa cttcgataaa   1500
aatctgccca tgaaaaagt gctcccgaag cacagcctcc tctacgagta cttcacggtg   1560
tacaacgagc tcacgaaggt gaagtacgtg accgagggta tgcggaagcc ggcgttcctg   1620
agcggcgagc agaagaaggc catcgtggac ctcctcttca agacgaaccg gaaagtcacc   1680
gtgaagcaat taaggagga ctacttcaag aaaatagagt gcttcgacag cgtcgagatc   1740
tcgggcgtcg aggacaggtt caacgcgtcg ctgggcacat accacgacct cctcaagatc   1800
attaaagaca aggacttcct ggacaacgag gagaacgagg acatcctcga ggacatcgtg   1860
ctgaccctca ccctgtttga ggaccggag atgatcgagg agcgcctcaa gacgtacgct   1920 cacctttcg acgacaaggt gatgaaacag ctgaagcggc gccgctacac cggatggggc   1980
cggctctccc gcaagctcat taatgggatc agggacaagc agtccggcaa gaccatactc   2040
gatttcctga gagcgacgg cttcgccaac cggaacttca tgcagctcat ccacgacgac   2100
tccctcactt tcaaggagga catccagaag gcccaggtca gcggacaggg cgactcgctc   2160
cacgaacaca tcgccaacct ggccgggtcg cctgcgatta aaaagggaat ccttcagacc   2220
gtcaaggtcg tggacgagct ggtgaaggtg atgggcaggc acaagcccga aaatatcgtc   2280
attgagatgg cccgggagaa ccagaccacg cagaaaggcc agaagaacag ccgggagcgc   2340
atgaaacgga tcgaggaggg tatcaaggag ctgggctcgc agatcctcaa ggagcaccct   2400
gtggaaaata cccagctgca gaatgaaaag ctctacctct actacctcca gaacggccgc   2460
gacatgtacg tggaccagga gctggacatt aatcgcctct cggactacga cgtcgaccac   2520
atcgtcccgc agtccttcct gaaggacgac agcatcgaca caaggtcttt gacccgctcc   2580
gataaaaatc gcgggaagtc cgacaacgtg ccgtcggagg aggtggtcaa gaagatgaaa   2640
aactactggc gccagctgct caacgccaag ctaatcacgc agcgcaagtt cgacaacctc   2700
accaaggccg aacgcggcgg tctctccgag cttgataagg ctgggttcat caagagacag   2760
ctggtggaga cccggcagat caccaagcat gtcgcccaga tcctggactc gcgcatgaat   2820
actaagtacg atgaaaacga caagctcatc cgcgaggtga aggtgatcac cctgaagagc   2880
aagctggtct cggacttccg gaaggacttc cagttctaca aggtccggga gatcaacaac   2940
```

| | |
|---|---|
| taccaccacg cgcacgacgc ctacctgaac gcggtggtgg gcacagccct tataaagaag | 3000 |
| taccctaagc tcgagtccga gttcgtgtac ggcgactaca aggtgtacga cgtccgcaag | 3060 |
| atgatcgcga agagcgagca ggagatcggg aaggccaccg caaaatactt cttctactcc | 3120 |
| aacatcatga acttcttcaa gaccgagatc accctggcca acggggagat ccgcaagcgc | 3180 |
| ccgctgattg agacgaacgg agagacaggc gagatagtct gggacaaggg cagggacttc | 3240 |
| gccaccgtgc gcaaggttct gtccatgccg caggtgaaca tcgtgaagaa gactgaggtg | 3300 |
| cagacaggcg gcttctcgaa ggagtccatc ctgcccaagc ggaacagcga caagctcatc | 3360 |
| gcgcggaaga aggactggga ccctaaaaaa tatggcgggt tcgactcgcc caccgtggct | 3420 |
| tactcggtcc tcgtggtggc caaggtcgag aagggcaaaa gcaagaagct gaagagcgtc | 3480 |
| aaggagctcc tcggcatcac catcatggag cggtccagct tcgagaagaa cccgatcgac | 3540 |
| ttcctcgagg cgaagggata taaggaggtg aagaaggacc tcatcattaa actgccgaag | 3600 |
| tactcgctat tcgaactgga gaatggtcgc aagaggatgc tcgcgagcgc tggcgagctg | 3660 |
| cagaaaggga acgagctggc tctcccgagc aagtacgtca acttcctcta cctggcctcc | 3720 |
| cactatgaaa agctcaaggg ctcgccggag gacaacgagc agaagcagct gttcgtcgag | 3780 |
| cagcacaagc attacctcga cgagatcatc gagcagatct cggagttcag caagcgcgtg | 3840 |
| atcctggccg acgccaacct cgacaaggtg ctgtccgcat ataacaagca ccgcgacaaa | 3900 |
| ccaatacggg agcaggccga aaatatcatc cacctgttca ccctcacgaa cctgggcgcc | 3960 |
| cccgccgcgt tcaagtactt cgacacaacc atcgaccgca agcggtacac gagcacgaag | 4020 |
| gaggtgctgg acgccacgtt gattcaccag tccatcacgg gcctgtatga aacaaggatc | 4080 |
| gatctcagcc agctcggcgg cgactag | 4107 |

```
<210> SEQ ID NO 5
<211> LENGTH: 21
<212> TYPE: DNA
<213> ORGANISM: Artificial Sequence
<220> FEATURE:
<223> OTHER INFORMATION: NLS

<400> SEQUENCE: 5
```

| | |
|---|---|
| ccgaagaaga agaggaaggt g | 21 |

```
<210> SEQ ID NO 6
<211> LENGTH: 1000
<212> TYPE: DNA
<213> ORGANISM: Zea mays

<400> SEQUENCE: 6
```

| | |
|---|---|
| tgagagtaca atgatgaacc tagattaatc aatgccaaag tctgaaaaat gcaccctcag | 60 |
| tctatgatcc agaaaatcaa gattgcttga ggccctgttc ggttgttccg gattagagcc | 120 |
| ccggattaat tcctagccgg attacttctc taatttatat agattttgat gagctggaat | 180 |
| gaatcctggc ttattccggt acaaccgaac aggccctgaa ggataccagt aatcgctgag | 240 |
| ctaaattggc atgctgtcag agtgtcagta ttgcagcaag gtagtgagat aaccggcatc | 300 |
| atggtgccag tttgatggca ccattagggt tagagatggt ggccatgggc gcatgtcctg | 360 |
| gccaactttg tatgatatat ggcagggtga ataggaaagt aaaattgtat tgtaaaaagg | 420 |
| gatttcttct gtttgttagc gcatgtacaa ggaatgcaag ttttgagcga ggggcatca | 480 |
| aagatctggc tgtgttttcca gctgtttttg ttagccccat cgaatccttg acataatgat | 540 |
| cccgcttaaa taagcaacct cgcttgtata gttccttgtg ctctaacaca cgatgatgat | 600 |

```
aagtcgtaaa atagtggtgt ccaaagaatt tccaggccca gttgtaaaag ctaaaatgct    660
attcgaattt ctactagcag taagtcgtgt ttagaaatta ttttttttata tacctttttt    720 ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt                         1000
```

<210> SEQ ID NO 7
<211> LENGTH: 19
<212> TYPE: DNA
<213> ORGANISM: Artificial Sequence
<220> FEATURE:
<223> OTHER INFORMATION: Guide

<400> SEQUENCE: 7
gggctgtgct acaacgtcg                                                  19

<210> SEQ ID NO 8
<211> LENGTH: 19
<212> TYPE: DNA
<213> ORGANISM: Artificial Sequence
<220> FEATURE:
<223> OTHER INFORMATION: Guide

<400> SEQUENCE: 8
gcgacgttgt agcacagcc                                                  19

<210> SEQ ID NO 9
<211> LENGTH: 18
<212> TYPE: DNA
<213> ORGANISM: Artificial Sequence
<220> FEATURE:
<223> OTHER INFORMATION: Guide

<400> SEQUENCE: 9
gcgtcgtggg acaacccc                                                   18

<210> SEQ ID NO 10
<211> LENGTH: 159
<212> TYPE: DNA
<213> ORGANISM: Artificial Sequence
<220> FEATURE:
<223> OTHER INFORMATION: Oligo

<400> SEQUENCE: 10
caacaacctg acggggacgc tggagttctc ggccgggttc taccagcgca tggggcggcg     60
gttcgcgtcg tgggacaacc ccggtctgta ctacaacgtc gcggccgtgg acgcggccca    120
cgcgccgtcg ggcgtggtgg tgtgcaagga cctgcagga                           159

<210> SEQ ID NO 11
<211> LENGTH: 159
<212> TYPE: DNA
<213> ORGANISM: Artificial Sequence
<220> FEATURE:
<223> OTHER INFORMATION: Oligo

<400> SEQUENCE: 11
caacaacctg acggggacgc tggagttctc ggccgggttc taccagcgca tggggcggcg     60

```
gttcgcgtcg tgggataacc caggtctgta ctacaacgtc gcggccgtgg acgcggccca      120
cgcgccgtcg ggcgtggtgg tgtgcaagga cctgcagga                            159
```

<210> SEQ ID NO 12
<211> LENGTH: 159
<212> TYPE: DNA
<213> ORGANISM: Artificial Sequence
<220> FEATURE:
<223> OTHER INFORMATION: Oligo

<400> SEQUENCE: 12

```
caacaacctg acggggacgc tggagttctc ggccgggttc taccagcgca tggggcggcg      60
gttcgcgtcg tgggataacc cagggctgta ctacaacgtc gcggccgtgg acgcggccca     120
cgcgccgtcg ggcgtggtgg tgtgcaagga cctgcagga                            159
```

<210> SEQ ID NO 13
<211> LENGTH: 146
<212> TYPE: DNA
<213> ORGANISM: Artificial Sequence
<220> FEATURE:
<223> OTHER INFORMATION: Oligo

<400> SEQUENCE: 13

```
gggacgctgg agttctcggc cgggttctac cagcgcatgg ggcggcggtt cgcgtcgtgg      60
gacaacccag gctgtactac aacgtcgcg ccgtggacg cggcccacgc gccgtcgggc      120
gtggtggtgt gcaaggacct gcagga                                          146
```

<210> SEQ ID NO 14
<211> LENGTH: 146
<212> TYPE: DNA
<213> ORGANISM: Artificial Sequence
<220> FEATURE:
<223> OTHER INFORMATION: Oligo

<400> SEQUENCE: 14

```
gggacgctgg agttctcggc cgggttctac cagcgcatgg ggcggcggtt cgcgtcgtgg      60
gacaacccag gctgtacta taacgtagcg ccgtggacg cggcccacgc gccgtcgggc      120
gtggtggtgt gcaaggacct gcagga                                          146
```

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15

```
atcgggaagc tgaagcagca tcggcgcgct gta                                   33
```

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16

```
atccgacggt agtgtttcgt cccgtcctcc tccg                                  34
```

<210> SEQ ID NO 17
<211> LENGTH: 58

```
<212> TYPE: DNA
<213> ORGANISM: Artificial Sequence
<220> FEATURE:
<223> OTHER INFORMATION: Primer

<400> SEQUENCE: 17
aatgatacgg cgaccaccga gatctacaca tacgagatcc gtaatcggga agctgaag      58

<210> SEQ ID NO 18
<211> LENGTH: 56
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(32)
<223> OTHER INFORMATION: n is a, c, g, or t

<400> SEQUENCE: 18
caagcagaag acggcatacg agatnnnnnn nnacacgcac gatccgacgg tagtgt        56

<210> SEQ ID NO 19
<211> LENGTH: 2592
<212> TYPE: DNA
<213> ORGANISM: Zea mays

<400> SEQUENCE: 19
atgaggcgcg ctcgcggtcg ccgcgggctg ctgcttctcc tcggcgtggc gctctcggcg      60
gctgcgctgc tccgtggctg cgcggggcag caagggagg acggctcgga cgcccctgcg     120
gcggcggcgg cggagacggc ccccatggag gagaaggagc gcagggcgct gtacgccgcc     180
atcgagagct tcgtcggcaa ggggtggaac ggctccgggc tctacccaga ccctgcggc     240 tggtctccca tccaggcgcg tccctgccct tcctgcgctt tcccttccgc atcgatctat     300
gttaccgtgc tgttcgattt tctggcccgc gtatgttcgt tcatcatgtt cgttcttcag     360
acgcgcgaag ctttcctctt tggtttttc ggctttgccc gtcctcgtca cacgcccttt      420
ctcggtgctc ccctgctgcc tgctttgagc tccaatccaa aaaccgtttg cgagcgaaag     480
gaggagcaag tcggtagcct ccgaaatgaa attggtgccc tgtttgggga tgcaggacgc     540
acgccaagtc gccaccaaat ctcctgctgt aatttcccgt gttaaaacct tcctcgtctc     600
gcttccagaa tttctggcct tccggtagcc tctgctgttt ttgtcttgtg ttcgtccttc     660
gtcgcactcg tgccctgctc ctcaactgtt gcttcgagat tgtggcactg ttttgctgtg     720
cgccgctgca cattcagttc actgttggac gagacctctg cttgatcccc ttgtgtcttc     780
gcatctcagc cttttgctcg atatggtagg aggatctgat ctcttgggca ggaactttcc     840
actcacatga aaagaacctc ccatgatttg aaatggcatg ctccgcccaa gattttttctc    900 atacagtact actactctct agtatagatt ttagtagtac cttgacatct tcttcctttt     960
gctcgcgccc gagaaggaat cagtcctact actccatagg agtttttgct ctaacaatta    1020
ctggaattta ccgcatattt atcttccttc acacggtaca ctggaatttc attctggttg    1080
ttacagtacc agtaaagtta agaaggggcc aaatttgtac taggtgcacc tttaagaaat    1140
gtcgccatct tggatcatcc tcatccatgt ctgttattac tgctagtagt tactgttgag    1200
cttgtgttta ctttccgagt aggacactct cagattgcag cgtgcttgcc tgcctgttaa    1260
aattaagggg attcaatttc agtggattga gcagatgtgg ttcttggatg ccaaaaacct    1320 gtgcagggggg tgtcatgtga tctcttcaat ggcctgtggt acccaacagt gatgagcatt    1380
```

| | |
|---|---|
| ggcccagtcc ttgacaactc gctgcagtgc ggccccgacg ccaagttcag cgcccagctg | 1440 |
| ttcgacctga ggcgcctccg gacgctgtct ttctacagct gcttcccggc gagcaacccc | 1500 |
| acggccatcc cgaccggcag ctgggagaag ctggcgggga cgctggagac gctggagttc | 1560 |
| cgcaccaacc cgggcctgaa cggcgccatc ccggcgtccc tcggccgcct ggccagcctg | 1620 |
| cagtcgctgg tgctcgtgga gaacaacctg acggggcccg tgcccgcgga ctgggcgcg | 1680 |
| ctgtcgaggc tgagacggct ggtgctgtcc gggaacgggc tgtcggggcc gatcccggtg | 1740 |
| acactcggta acgaccgccg cgccgacgag ctgctgctga tcgtggacct gagcaggaac | 1800 |
| tatctaaccg gctctctgcc ttcgtcgcta ggtggcctca cggggctcct gaagatggac | 1860 |
| ctgagcagca acctgctgca gggcagcatc ccgccggagc tcgcggggct caggagcctc | 1920 |
| acgctgctgg acctcaggaa caacagcctc accggcgggc tgccccagtt cgtgcagggc | 1980 |
| atggcgtcgc tgcaggacct gctgctctcg aacaacccgc tgggcggcgg cctgccgcag | 2040 |
| tccggctggg gggcgctggc gggcctggcc acgctggacc tgtccaacgt cggcctcgtg | 2100 |
| ggcgccatac cggggtccat ggcggccctg acggggctcc ggttcctggc gctggaccac | 2160 |
| aaccgcctga cggggggccgt gccgcccgag ctcgcccggc tgcccagcat cggcgcgctg | 2220 |
| tacctgaacg caacaacct gacggggacg ctggagttct cggccgggtt ctaccagcgc | 2280 |
| atggggcggc ggttcgcgtc gtgggacaac cccgggctgt gctacaacgt cgcggccgtg | 2340 |
| gacgcggccc acgcgccgtc gggcgtggtg gtgtgcaagg acctgcagga gcccagcgtg | 2400 |
| ggcggcggcg cgcgggacgg ggacggggac ggggacgcgg aggaggacgg gacgaagccc | 2460 |
| gaggcgggct ccagcctcgt ggcctcctcg tcgtccggca tgccggttgg cagtgtcggt | 2520 |
| gggctccggt acctggtggt ggttcgggga atggcggctg cggttcttgg gttggtgtcc | 2580 |
| ctcctacaat ag | 2592 |

```
<210> SEQ ID NO 20
<211> LENGTH: 77
<212> TYPE: DNA
<213> ORGANISM: Artificial Sequence
<220> FEATURE:
<223> OTHER INFORMATION: Guide

<400> SEQUENCE: 20
```

| | |
|---|---|
| gttttagagc tagaaatagc aagttaaaat aaggctagtc cgttatcaac ttgaaaaagt | 60 |
| ggcaccgagt cggtgct | 77 |

```
<210> SEQ ID NO 21
<211> LENGTH: 490
<212> TYPE: PRT
<213> ORGANISM: Zea mays

<400> SEQUENCE: 21
```

```
Ala Leu Ser Ala Ala Ala Leu Leu Arg Gly Cys Ala Gly Gln Gln Gly
1               5                   10                  15

Glu Asp Gly Ser Asp Ala Pro Ala Ala Ala Ala Glu Thr Ala Pro
            20                  25                  30

Met Glu Glu Lys Glu Arg Arg Ala Leu Tyr Ala Ala Ile Glu Ser Phe
        35                  40                  45

Val Gly Lys Gly Trp Asn Gly Ser Gly Leu Tyr Pro Asp Pro Cys Gly
    50                  55                  60

Trp Ser Pro Ile Gln Gly Val Ser Cys Asp Leu Phe Asn Gly Leu Trp
65                  70                  75                  80
```

```
Tyr Pro Thr Val Met Ser Ile Gly Pro Val Leu Asp Asn Ser Leu Gln
             85                  90                  95

Cys Gly Pro Asp Ala Lys Phe Ser Ala Gln Leu Phe Asp Leu Arg Arg
            100                 105                 110

Leu Arg Thr Leu Ser Phe Tyr Ser Cys Phe Pro Ala Ser Asn Pro Thr
            115                 120                 125

Ala Ile Pro Thr Gly Ser Trp Glu Lys Leu Ala Gly Thr Leu Glu Thr
            130                 135                 140

Leu Glu Phe Arg Thr Asn Pro Gly Leu Asn Gly Ala Ile Pro Ala Ser
145                 150                 155                 160

Leu Gly Arg Leu Ala Ser Leu Gln Ser Leu Val Leu Glu Asn Asn
            165                 170                 175

Leu Thr Gly Pro Val Pro Ala Glu Leu Gly Ala Leu Ser Arg Leu Arg
            180                 185                 190

Arg Leu Val Leu Ser Gly Asn Gly Leu Ser Gly Pro Ile Pro Val Thr
            195                 200                 205

Leu Gly Asn Asp Arg Arg Ala Asp Glu Leu Leu Leu Ile Val Asp Leu
            210                 215                 220

Ser Arg Asn Tyr Leu Thr Gly Ser Leu Pro Ser Ser Leu Gly Gly Leu
225                 230                 235                 240

Thr Gly Leu Leu Lys Met Asp Leu Ser Ser Asn Leu Leu Gln Gly Ser
            245                 250                 255

Ile Pro Pro Glu Leu Ala Gly Leu Arg Ser Leu Thr Leu Leu Asp Leu
            260                 265                 270

Arg Asn Asn Ser Leu Thr Gly Gly Leu Pro Gln Phe Val Gln Gly Met
            275                 280                 285

Ala Ser Leu Gln Asp Leu Leu Leu Ser Asn Asn Pro Leu Gly Gly Gly
            290                 295                 300

Leu Pro Gln Ser Gly Trp Gly Ala Leu Ala Gly Leu Ala Thr Leu Asp
305                 310                 315                 320

Leu Ser Asn Val Gly Leu Val Gly Ala Ile Pro Gly Ser Met Ala Ala
            325                 330                 335

Leu Thr Gly Leu Arg Phe Leu Ala Leu Asp His Asn Arg Leu Thr Gly
            340                 345                 350

Ala Val Pro Pro Glu Leu Ala Arg Leu Pro Ser Ile Gly Ala Leu Tyr
            355                 360                 365

Leu Asn Gly Asn Asn Leu Thr Gly Thr Leu Glu Phe Ser Ala Gly Phe
            370                 375                 380

Tyr Gln Arg Met Gly Arg Arg Phe Ala Ser Trp Asp Asn Pro Gly Leu
385                 390                 395                 400

Cys Tyr Asn Val Ala Ala Val Asp Ala Ala His Ala Pro Ser Gly Val
            405                 410                 415

Val Val Cys Lys Asp Leu Gln Glu Pro Ser Val Gly Gly Ala Arg
            420                 425                 430

Asp Gly Asp Gly Asp Gly Asp Ala Glu Glu Asp Gly Thr Lys Pro Glu
            435                 440                 445

Ala Gly Ser Ser Leu Val Ala Ser Ser Ser Gly Met Pro Val Gly
            450                 455                 460

Ser Val Gly Gly Leu Arg Tyr Leu Val Val Val Arg Gly Met Ala Ala
465                 470                 475                 480

Ala Val Leu Gly Leu Val Ser Leu Leu Gln
            485                 490
```

```
<210> SEQ ID NO 22
<211> LENGTH: 463
<212> TYPE: PRT
<213> ORGANISM: Zea mays

<400> SEQUENCE: 22
```

| | | | | | | | | | | | | | | | |
|---|---|---|---|---|---|---|---|---|---|---|---|---|---|---|---|
| Ala | Leu | Ser | Ala | Ala | Leu | Leu | Arg | Gly | Cys | Ala | Gly | Gln | Gln | Gly | |
| 1 | | | | 5 | | | | | 10 | | | | | 15 | |
| Glu | Asp | Gly | Ser | Asp | Ala | Pro | Ala | Ala | Ala | Ala | Glu | Thr | Ala | Pro | |
| | | | 20 | | | | | 25 | | | | | 30 | | |
| Met | Glu | Glu | Lys | Glu | Arg | Arg | Ala | Leu | Tyr | Ala | Ala | Ile | Glu | Ser | Phe |
| | | | 35 | | | | | 40 | | | | | 45 | | |
| Val | Gly | Lys | Gly | Trp | Asn | Gly | Ser | Gly | Leu | Tyr | Pro | Asp | Pro | Cys | Gly |
| 50 | | | | | 55 | | | | | 60 | | | | | |
| Trp | Ser | Pro | Ile | Gln | Gly | Val | Ser | Cys | Asp | Leu | Phe | Asn | Gly | Leu | Trp |
| 65 | | | | | 70 | | | | | 75 | | | | | 80 |
| Tyr | Pro | Thr | Val | Met | Ser | Ile | Gly | Pro | Val | Leu | Asp | Asn | Ser | Leu | Gln |
| | | | | 85 | | | | | 90 | | | | | 95 | |
| Cys | Gly | Pro | Asp | Ala | Lys | Phe | Ser | Ala | Gln | Leu | Phe | Asp | Leu | Arg | Arg |
| | | | 100 | | | | | 105 | | | | | 110 | | |
| Leu | Arg | Thr | Leu | Ser | Phe | Tyr | Ser | Cys | Phe | Pro | Ala | Ser | Asn | Pro | Thr |
| | | | 115 | | | | | 120 | | | | | 125 | | |
| Ala | Ile | Pro | Thr | Gly | Ser | Trp | Glu | Lys | Leu | Ala | Gly | Thr | Leu | Glu | Thr |
| | 130 | | | | | 135 | | | | | 140 | | | | |
| Leu | Glu | Phe | Arg | Thr | Asn | Pro | Gly | Leu | Asn | Gly | Ala | Ile | Pro | Ala | Ser |
| 145 | | | | | 150 | | | | | 155 | | | | | 160 |
| Leu | Gly | Arg | Leu | Ala | Ser | Leu | Gln | Ser | Leu | Val | Leu | Val | Glu | Asn | Asn |
| | | | | 165 | | | | | 170 | | | | | 175 | |
| Leu | Thr | Gly | Pro | Val | Pro | Ala | Glu | Leu | Gly | Ala | Leu | Ser | Arg | Leu | Arg |
| | | | 180 | | | | | 185 | | | | | 190 | | |
| Arg | Leu | Val | Leu | Ser | Gly | Asn | Gly | Leu | Ser | Gly | Pro | Ile | Pro | Val | Thr |
| | | 195 | | | | | 200 | | | | | 205 | | | |
| Leu | Gly | Gly | Gly | Leu | Thr | Gly | Leu | Leu | Lys | Met | Asp | Leu | Ser | Ser | Asn |
| 210 | | | | | 215 | | | | | 220 | | | | | |
| Leu | Leu | Gln | Gly | Ser | Ile | Pro | Pro | Glu | Leu | Ala | Gly | Leu | Arg | Ser | Leu |
| 225 | | | | | 230 | | | | | 235 | | | | | 240 |
| Thr | Leu | Leu | Asp | Leu | Arg | Asn | Asn | Ser | Leu | Thr | Gly | Gly | Leu | Pro | Gln |
| | | | | 245 | | | | | 250 | | | | | 255 | |
| Phe | Val | Gln | Gly | Met | Ala | Ser | Leu | Gln | Asp | Leu | Leu | Leu | Ser | Asn | Asn |
| | | | 260 | | | | | 265 | | | | | 270 | | |
| Pro | Leu | Gly | Gly | Gly | Leu | Pro | Gln | Ser | Gly | Trp | Gly | Ala | Leu | Ala | Gly |
| | | 275 | | | | | 280 | | | | | 285 | | | |
| Leu | Ala | Thr | Leu | Asp | Leu | Ser | Asn | Val | Gly | Leu | Val | Gly | Ala | Ile | Pro |
| | 290 | | | | | 295 | | | | | 300 | | | | |
| Gly | Ser | Met | Ala | Ala | Leu | Thr | Gly | Leu | Arg | Phe | Leu | Ala | Leu | Asp | His |
| 305 | | | | | 310 | | | | | 315 | | | | | 320 |
| Asn | Arg | Leu | Thr | Gly | Ala | Val | Pro | Pro | Glu | Leu | Ala | Arg | Leu | Pro | Ser |
| | | | | 325 | | | | | 330 | | | | | 335 | |
| Ile | Gly | Ala | Leu | Tyr | Leu | Asn | Gly | Asn | Asn | Leu | Thr | Gly | Thr | Leu | Glu |
| | | | 340 | | | | | 345 | | | | | 350 | | |
| Phe | Ser | Ala | Gly | Phe | Tyr | Gln | Arg | Met | Gly | Arg | Arg | Phe | Ala | Ser | Trp |
| | | 355 | | | | | 360 | | | | | 365 | | | |
| Asp | Asn | Pro | Gly | Leu | Cys | Tyr | Asn | Val | Ala | Ala | Val | Asp | Ala | Ala | His |
| | 370 | | | | | 375 | | | | | 380 | | | | |

Ala Pro Ser Gly Val Val Cys Lys Asp Leu Gln Glu Pro Ser Val
385                 390                 395                 400

Gly Gly Gly Ala Arg Asp Gly Asp Gly Asp Ala Glu Glu Asp
            405                 410                 415

Gly Thr Lys Pro Glu Ala Gly Ser Ser Leu Val Ala Ser Ser Ser Ser
            420                 425                 430

Gly Met Pro Val Gly Ser Val Gly Gly Leu Arg Tyr Leu Val Val Val
            435                 440                 445

Arg Gly Met Ala Ala Val Leu Gly Leu Val Ser Leu Leu Gln
450                 455                 460

<210> SEQ ID NO 23
<211> LENGTH: 506
<212> TYPE: PRT
<213> ORGANISM: Zea mays

<400> SEQUENCE: 23

Met Arg Arg Ala Arg Gly Arg Gly Leu Leu Leu Leu Gly Val
1               5                   10                  15

Ala Leu Ser Ala Ala Leu Leu Arg Gly Cys Ala Gly Gln Gln Gly
                20                  25                  30

Glu Asp Gly Ser Asp Ala Pro Ala Ala Ala Ala Glu Thr Ala Pro
            35                  40                  45

Met Glu Glu Lys Glu Arg Arg Ala Leu Tyr Ala Ala Ile Glu Ser Phe
50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Gln
                100                 105                 110

Cys Gly Pro Asp Ala Lys Phe Ser Ala Gln Leu Phe Asp Leu Arg Arg
            115                 120                 125

Leu Arg Thr Leu Ser Phe Tyr Ser Cys Phe Pro Ala Ser Asn Pro Thr
130                 135                 140

Ala Ile Pro Thr Gly Ser Trp Glu Lys Leu Ala Gly Thr Leu Glu Thr
145                 150                 155                 160

Leu Glu Phe Arg Thr Asn Pro Gly Leu Asn Gly Ala Ile Pro Ala Ser
                165                 170                 175

Leu Gly Arg Leu Ala Ser Leu Gln Ser Leu Val Leu Val Glu Asn Asn
            180                 185                 190

Leu Thr Gly Pro Val Pro Ala Glu Leu Gly Ala Leu Ser Arg Leu Arg
            195                 200                 205

Arg Leu Val Leu Ser Gly Asn Gly Leu Ser Gly Pro Ile Pro Val Thr
210                 215                 220

Leu Gly Asn Asp Arg Arg Ala Asp Glu Leu Leu Leu Ile Val Asp Leu
225                 230                 235                 240

Ser Arg Asn Tyr Leu Thr Gly Ser Leu Pro Ser Ser Leu Gly Gly Leu
                245                 250                 255

Thr Gly Leu Leu Lys Met Asp Leu Ser Ser Asn Leu Leu Gln Gly Ser
            260                 265                 270

Ile Pro Pro Glu Leu Ala Gly Leu Arg Ser Leu Thr Leu Leu Asp Leu
            275                 280                 285

Arg Asn Asn Ser Leu Thr Gly Gly Leu Pro Gln Phe Val Gln Gly Met
290                 295                 300

```
Ala Ser Leu Gln Asp Leu Leu Ser Asn Asn Pro Leu Gly Gly Gly
305                 310                 315                 320

Leu Pro Gln Ser Gly Trp Gly Ala Leu Ala Gly Leu Ala Thr Leu Asp
            325                 330                 335

Leu Ser Asn Val Gly Leu Val Gly Ala Ile Pro Gly Ser Met Ala Ala
                340                 345                 350

Leu Thr Gly Leu Arg Phe Leu Ala Leu Asp His Asn Arg Leu Thr Gly
            355                 360                 365

Ala Val Pro Pro Glu Leu Ala Arg Leu Pro Ser Ile Gly Ala Leu Tyr
        370                 375                 380

Leu Asn Gly Asn Asn Leu Thr Gly Thr Leu Glu Phe Ser Ala Gly Phe
385                 390                 395                 400

Tyr Gln Arg Met Gly Arg Arg Phe Ala Ser Trp Asp Asn Pro Gly Leu
                405                 410                 415

Cys Tyr Asn Val Ala Ala Val Asp Ala Ala His Ala Pro Ser Gly Val
                420                 425                 430

Val Val Cys Lys Asp Leu Gln Glu Pro Ser Val Gly Gly Gly Ala Arg
            435                 440                 445

Asp Gly Asp Gly Asp Gly Asp Ala Glu Glu Asp Gly Thr Lys Pro Glu
        450                 455                 460

Ala Gly Ser Ser Leu Val Ala Ser Ser Ser Gly Met Pro Val Gly
465                 470                 475                 480

Ser Val Gly Gly Leu Arg Tyr Leu Val Val Val Arg Gly Met Ala Ala
                485                 490                 495

Ala Val Leu Gly Leu Val Ser Leu Leu Gln
            500                 505

<210> SEQ ID NO 24
<211> LENGTH: 478
<212> TYPE: PRT
<213> ORGANISM: Zea mays

<400> SEQUENCE: 24

Met Arg Arg Ala Arg Gly Arg Gly Leu Leu Leu Leu Gly Val
1               5                   10                  15

Ala Leu Ser Ala Ala Ala Leu Leu Arg Gly Cys Ala Gly Gln Gln Gly
                20                  25                  30

Glu Asp Gly Ser Asp Ala Pro Ala Ala Ala Ala Glu Thr Ala Pro
            35                  40                  45

Met Glu Glu Lys Glu Arg Arg Ala Leu Tyr Ala Ala Ile Glu Ser Phe
    50                  55                  60

Val Gly Lys Gly Trp Asn Gly Ser Gly Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Gln
                100                 105                 110

Cys Gly Pro Asp Ala Lys Phe Ser Ala Gln Leu Phe Asp Leu Arg Arg
            115                 120                 125

Leu Arg Thr Leu Ser Phe Tyr Ser Cys Phe Pro Ala Ser Asn Pro Thr
        130                 135                 140

Ala Ile Pro Thr Gly Ser Trp Glu Lys Leu Ala Gly Thr Leu Glu Thr
145                 150                 155                 160

Leu Glu Phe Arg Thr Asn Pro Gly Leu Asn Gly Ala Ile Pro Ala Ser
```

```
                    165                 170                 175
Leu Gly Arg Leu Ala Ser Leu Gln Ser Leu Val Leu Val Glu Asn Asn
            180                 185                 190
Leu Thr Gly Pro Val Pro Ala Glu Leu Gly Ala Leu Ser Arg Leu Arg
            195                 200                 205
Arg Leu Val Leu Ser Gly Asn Gly Leu Ser Gly Pro Ile Pro Val Thr
        210                 215                 220
Leu Gly Gly Leu Thr Gly Leu Leu Lys Met Asp Leu Ser Ser Asn Leu
225                 230                 235                 240
Leu Gln Gly Ser Ile Pro Pro Glu Leu Ala Gly Leu Arg Ser Leu Thr
                245                 250                 255
Leu Leu Asp Leu Arg Asn Asn Ser Leu Thr Gly Gly Leu Pro Gln Phe
            260                 265                 270
Val Gln Gly Met Ala Ser Leu Gln Asp Leu Leu Leu Ser Asn Asn Pro
            275                 280                 285
Leu Gly Gly Gly Leu Pro Gln Ser Gly Trp Gly Ala Leu Ala Gly Leu
        290                 295                 300
Ala Thr Leu Asp Leu Ser Asn Val Gly Leu Val Gly Ala Ile Pro Gly
305                 310                 315                 320
Ser Met Ala Ala Leu Thr Gly Leu Arg Phe Leu Ala Leu Asp His Asn
                325                 330                 335
Arg Leu Thr Gly Ala Val Pro Pro Glu Leu Ala Arg Leu Pro Ser Ile
            340                 345                 350
Gly Ala Leu Tyr Leu Asn Gly Asn Asn Leu Thr Gly Thr Leu Glu Phe
            355                 360                 365
Ser Ala Gly Phe Tyr Gln Arg Met Gly Arg Arg Phe Ala Ser Trp Asp
        370                 375                 380
Asn Pro Gly Leu Cys Tyr Asn Val Ala Ala Val Asp Ala Ala His Ala
385                 390                 395                 400
Pro Ser Gly Val Val Cys Lys Asp Leu Gln Glu Pro Ser Val Gly
                405                 410                 415
Gly Gly Ala Arg Asp Gly Asp Gly Asp Gly Asp Ala Glu Glu Asp Gly
            420                 425                 430
Thr Lys Pro Glu Ala Gly Ser Ser Leu Val Ala Ser Ser Ser Gly
        435                 440                 445
Met Pro Val Gly Ser Val Gly Gly Leu Arg Tyr Leu Val Val Arg
            450                 455                 460
Gly Met Ala Ala Ala Val Leu Gly Leu Val Ser Leu Leu Gln
465                 470                 475

<210> SEQ ID NO 25
<211> LENGTH: 3426
<212> TYPE: DNA
<213> ORGANISM: Zea mays

<400> SEQUENCE: 25
aattcatcat ccgatggtaa cgaggaagat gttttagctg tgggtgaaaa tagcacaccg      60
aacccaagca ttgtacttaa aggaagcgca aggtgtttca tgactctctg aagcctagga    120 tgaaaagaa acatagggat gactacatga aaggattgt cgatgccttt gagtcgagga      180
cctttagctc gaacaagacc atttcatcct atgacaatga tccggtgtgt aaggaggttg    240
ctgctcaatt gaagaatgtc atccaagatg gtgcaaccga aggaagcgac ttgcatttct    300
tcgcaactca attattaata gacaaacatc atcgggatgt ctttgcaact cttgagacaa    360
```

```
aggaaggaag gaacgcttgg cttcgtcgcg cgtacgataa tcatgacaag tcgagttagg    420
tcatttgttc ctgttggtgc cctggagctg aagcaaaatg tttcatgtta tcggtagtct    480
atagactgtt tggtgttctc gatcgtctat tttactttt ctagaactgt tggtcgttta    540
agtttgttat ctattggagt actgattcca tttttcggtt gaggtctttg ttttgaataa    600
aaacacttga gagtgacagt ggttatttgt atatgctaga gcaatagtgg ttatttgttg    660
ttaaacaatt tcagtactgt ttaaacgttt ctaatatgtg tttgcttcca tgtgtgctac    720
tggtaattag tattctatgc cacaattgta ttctggatga attaaacact agtatacttc    780
ttgtgtgtct gtagatggtg tagacaaatg atgaacaaaa tgatgacgaa attcatgagg    840
aatttatggt cgttgtagtt gcattggaga tgtgggggac tcctcagacg tggttgtacg    900
acaaccaatg gcagaaacat gtatacactg ggtcgatata accttagaga gtagtaatga    960
ttgctacgtc atgtttcgca tgcgtcggac tgtctttcat cgacttcatg acacattggt   1020
caacaattat ggtctagtag cgagtcaccg agttagtacg aaggaggcgc ttgctatttt   1080
tctgtgggcg tgcggggggg gttaatcatt tcgagagata ataaataagt ttggccattc   1140
attggaaact ataaaccata aatttagtga agtacttgac gcaatatata ggatgtccaa   1200
cgacgcgact aagcccaagg atgcccattt cactaatatt cacccaagac tacgggaggc   1260
tcggtttgac cacatttcaa ggactacata ggagctatcg ttggaagcca ttttcccgcc   1320
tctgtccctt tgtcggagca accaaaatat attggtcgtc acgggtacac atcgcagaat   1380
gtcatgatca tttgtgagtt cgaaatgagg tacacattta tcatcactgg ttggcctcgt   1440
tccgtgcatg atactagagt gctacaagat actctgatca cgtacgacga taggttcccg   1500
cattcttcag aagatattac tccaatctac gtctgtagta tttcgaagtc acctcgttat   1560
gtatgacctt aaccatgata attttatatt tcaggaaaat attatcttgt tgattcgggg   1620
tacctcaata ggacgggata ccttgcacct tataaaggtc aaaagtacca catttttcgaa   1680 tttaaggatg gaaggcaacc tgttgctacc aaagaggttt tcaactatgc gcacttgttc   1740
ccgaggaata ttatagagca atcatttggg gtgcccaaga taaattggag aattcttatt   1800
agcctacctt cattttcact gagaaagcaa tccaagataa ttatatcatg catgatgtta   1860
cataacttca ttcgggacag tgttttacac tttcgcgact tcgattagta tatacctgca   1920
tgaggcatgt tcaggatgta gctataggtg agagtagtag caaacgctag atgagttaga   1980
catatgtgct tttagagatt caagtgctaa tgtgttagtg tcatagttag ttatccgtac   2040
gagtaaataa acatgttgta atggacaaat catgtggtaa tttctaatta ggtgctaatt   2100
agtatgtatg tttttctttt ttttcatttt ctactatctt agaatcagtc tatccaaaca   2160
cctaaattct aaccaccagc ttcttcccat agcacctaaa ccaaatactc agattcttct   2220
tcttcatagt cagattctct ctacaaccat tttttcaaaa aagctgaatc aaacagactc   2280
atagacacac gatgttcttg tctatttta tctttagtac tagtttgaca attctatta     2340 aaaaaaacta ttttctcgag ataaattagc tggaaatctc ttagactaac tccaacagag   2400
cagccaaagc caatatggct gtcgtggtgc tactgtagcg cctagaaaca ggttccaaca   2460
acacagccaa aaggagcagc tattttagag gggatgagag agaaaagcta gattggctgg   2520
ttcagagccg gcagccattt tctccccttc gtctctgaca atccggaccc acttctgagg   2580
cttctggcca ctcgccctgg gaaccagcta ttttagctgc tccgttggat acgaaggacg   2640 tatgatggc cagctaaatt actgtggcaa gccaacggcc tgaatgtctg cccgttttgg    2700
ctagtgcctg ttggagacag ccttaggagt tgacaaacta ggggctagtt tggatcggca   2760
```

```
cgccggcggc cacgccgcgc cacacctgtg gcgctgaaaa cgagcgccac actggtggcg      2820
tgggaagtgt ggcgggcggc ggcggcttag gcggccatcc aaacatcccc tagaccttaa      2880
ccaaacattc ctcccttctc gcttgtgtgt aacacccact ccgtattttt caccagcgcc      2940
accacggtaa agtgcacgct gttcctgcgg gacattacta caaaaccaat cccccgtctt      3000
gcgaggtcgc gagtctctcc aactccgtcc ctctggcctc agcacaacgc cagaccgcct      3060
gcctgtgctt gcagccaggc cggccagctg cctgcctgcc tgttgtcgtc tgcggcgcga      3120
cggcggccgc ccggtcgacc gcccgcattg ggatccccag agcagcgctt ggcataggggg     3180 aatgtcccgg gtcagccacc gtcgcctctg cgctgcgaaa gccccgcatt tacttgccac      3240
ctagaagggg gcacccctcg cgagacccag cgccagacag agccagcaat ggctgctgct      3300
gctgctcctc ctcctcctat atagcggggc ccgtgccgag cgctcgatcc agttcttctg      3360
atctctgact tctgagcgag gagtggacga gtggtgtgcc gtcgtccggt tcccgttggt      3420
ttggcg                                                                3426
```

```
<210> SEQ ID NO 26
<211> LENGTH: 1295
<212> TYPE: DNA
<213> ORGANISM: Zea mays

<400> SEQUENCE: 26
tagcaagcaa gcaggttcag aagaagaaca cggagaaact tgaagtaatg ctaggtaggt        60
tagcacgaag tagtttctgc gcgttctctg tgatcttttg gcatttgttt ttggctgctg       120
gtggcttacc atcgtcagat ggtgacggag gaaggaggga acatggatct ggatggtgtg       180
agccacagat tacattacag tagtagagta aactatgaga gttcttgtgg actgaaggtg       240
tgtagtggtg gatagggtag cttctccggg gttctttgt gtgtaattag cctgtgtcgc        300
cctgtggtgt catgttacaa cagcaagtgg aaatctaagc tggttcgtcc gttgttggag       360
aatcagaaaa aaaaaaattg tcgtgcttca ttcacatcac atggatacac agtttcctgt       420
tcttggagca gaagaactgg aaagatctct cgttatctct atttgctata gaaagaacat       480
agcggcggta tctgcagacg atacaaatgg aagaagagcg ggcaagcagc acgacaggat      540
ggagcggcgg cgccgccgca tatgtccggc tgccgcctgc cggcgatctc ggtgtctcct       600
gctgcctttt gcctttgcgt gttctcgagt ctgaaaataa aatcaaaaat atggaccgag       660
acgctgattg cgcagggccc cgcgctcgca gaggagtcag aaacagaaag gacctgtcac       720
cttggaaagc tggcggccgg agcggagccc tcacagacag gctgcgctct gcctctctgg       780
cactggcagg cggcagcggc agtagcgcta gtcctctaca ggtggaggct ggactgcacc       840
tcgacgtgta ggaactgtag cgtcattgtg gtactccggc gtctgtaccg gtctactcta       900 cactttttcca tcccagtacg ctttgaaata tttacaaaaa ataaatgtat ttaatgatga      960
tatcactagc tctagttgtc ttttttttta tttatcttc tcttaaaata caacaagtac       1020
actattatag atatataatt tatcactaac attatttatt ttgaaaacga gggagcaccg      1080
gagcagtact ctgtactcct agtgctacgc aatggcgcgg tggcaccacg caccaggcac      1140
cagcctgcgg gtgcaggtat aggcgtgcta gcacctagca gtatgggggtt gggctgcacg     1200 tcgcagtact agcgcgtaga agcaatcgat gctctcgccg aaaaacaaag gcacaggatc     1260
agtggcacag ctcgtaatac aattgtcgtt tcctc                                1295
```

```
<210> SEQ ID NO 27
```

```
<211> LENGTH: 477
<212> TYPE: PRT
<213> ORGANISM: Oryza sativa

<400> SEQUENCE: 27

Met Arg Gln Pro Gln Ser Arg Lys Leu Leu Gln Leu Gln Ala Leu Ser
1               5                   10                  15

Leu Leu Leu Phe Ile Ile Ala Leu His Ser Arg Leu His Gly Cys Ser
            20                  25                  30

Gly Gln Gly Glu Ala Ala Asp Gly Ser Ala Ser Thr Ala Ala Ala Pro
        35                  40                  45

Met Glu Glu Lys Glu Lys Arg Ala Leu Tyr Ala Ala Ile Glu Gly Phe
50                  55                  60

Val Gly Lys Gly Trp Asn Gly Ser Ala Leu Tyr Pro Asp Pro Cys Gly
65                  70                  75                  80

Trp Ser Pro Ile Gln Gly Val Ser Cys Asp Leu Phe Asn Gly Leu Trp
                85                  90                  95

Tyr Pro Thr Val Met Ser Ile Gly Pro Val Leu Asp Asn Ser Leu Arg
            100                 105                 110

Cys Ser Ala Asp Ala Lys Phe Ser Pro Gln Leu Phe Asp Leu Lys Arg
        115                 120                 125

Leu Lys Thr Leu Ser Phe Tyr Ser Cys Phe Pro Ala Thr Asn Pro Thr
130                 135                 140

Pro Ile Pro Ala Thr Ser Trp Asp Lys Leu Ala Gly Ser Leu Glu Thr
145                 150                 155                 160

Leu Glu Phe Arg Thr Asn Pro Gly Leu Thr Gly Pro Ile Pro Ala Ser
                165                 170                 175

Leu Gly Arg Leu Ser Ser Leu Gln Ser Leu Val Phe Val Glu Asn Asn
            180                 185                 190

Leu Thr Gly Ala Val Pro Ala Glu Leu Gly Ser Leu Val Arg Leu Arg
        195                 200                 205

Arg Leu Val Leu Ser Gly Asn Gly Leu Ser Gly Gln Ile Pro Ala Ser
210                 215                 220

Leu Gly Asn Gly His Phe Ala Glu Gln Leu Leu Ile Met Asp Val Ser
225                 230                 235                 240

Asn Asn Ser Leu Thr Gly Ser Leu Pro Ser Ser Leu Gly Gly Leu Lys
                245                 250                 255

Gly Leu Leu Lys Met Asp Leu Ser Asn Asn Leu Leu Gln Gly Ser Leu
            260                 265                 270

Pro Pro Glu Leu Ala Gly Leu Gly Ser Leu Thr Leu Leu Asp Leu Arg
        275                 280                 285

Asn Asn Ser Phe Thr Gly Gly Leu Pro Ser Phe Leu Gln Gly Met Ala
290                 295                 300

Ser Leu Gln Asp Leu Leu Ser Asn Asn Pro Leu Gly Gly Ser Leu
305                 310                 315                 320

Gly Gln Leu Gly Trp Glu Arg Leu Arg Gly Leu Ala Thr Leu Asp Leu
                325                 330                 335

Ser Asn Leu Gly Leu Val Gly Ala Ile Pro Glu Ser Met Ala Ala Leu
            340                 345                 350

Thr Arg Leu Arg Phe Leu Ala Leu Asp His Asn Arg Leu Thr Gly Asp
        355                 360                 365

Val Pro Ala Arg Leu Ala Glu Leu Pro Asn Ile Gly Ala Leu Tyr Leu
370                 375                 380

Asn Gly Asn Asn Leu Thr Gly Thr Leu Gln Phe Ser Pro Ala Phe Tyr
```

```
                    385                 390                 395                 400
            Gln Arg Met Gly Arg Arg Phe Ala Ser Trp Asp Asn Pro Gly Leu Cys
                            405                 410                 415

Tyr Ser Asn Ala Ala Val Asp Ala Ala His Ala Pro Pro Gly Val Thr
                            420                 425                 430

Val Cys Lys Val Ala Gly Gly Val Gly Asp Gly Arg Lys Pro Glu Ala
                            435                 440                 445

Ser Ser Ser Leu Met Ala Thr Ser Ser Ala Ser Asn Leu Ile Asn Gly
                    450                 455                 460

Phe Cys Phe Phe Leu Trp Met Val Ala Thr Ser Leu Leu
            465                 470                 475

<210> SEQ ID NO 28
<211> LENGTH: 1521
<212> TYPE: DNA
<213> ORGANISM: Zea mays

<400> SEQUENCE: 28
atgaggcgcg ctcgcggtcg ccgcgggctg ctgcttctcc tcggcgtggc gctctcggcg       60
gctgcgctgc tccgtggctg cgcggggcag caaggggagg acggctcgga cgcccctgcg      120
gcggcggcgg cggagacggc ccccatggag agaaggagc gcagggcgct gtacgccgcc       180
atcgagagct tcgtcggcaa ggggtggaac ggctccgggc tctacccaga ccctgcggc       240 tggtctccca tccagggggt gtcatgtgat ctcttcaatg gcctgtggta cccaacagtg      300
atgagcattg gccagtcct tgacaactcg ctgcagtgcg ccccgacgc caagttcagc        360 gcccagctgt tcgacctgag cgcctccgg acgctgtctt tctacagctg cttcccggcg       420
agcaacccca cggccatccc gaccggcagc tgggagaagc tggcggggac gctggagacg      480
ctggagttcc gcaccaaccc gggcctgaac ggcgccatcc cggcgtccct cggccgcctg      540
gccagcctgc agtcgctggt gctcgtggag aacaacctga cggggcccgt gcccgcggag      600
ctgggcgcgc tgtcgaggct gagacggctg gtgctgtccg ggaacgggct gtcggggccg      660
atcccggtga cactcggtaa cgaccgccgc cgacgagc tgctgctgat cgtggacctg        720
agcaggaact atctaaccgg ctctctgcct tcgtcgctag gtggcctcac ggggctcctg      780
aagatggacc tgagcagcaa cctgctgcag ggcagcatcc cgccggagct cgcggggctc      840
aggagcctca cgctgctgga cctcaggaac aacagcctca ccggcgggct gccccagttc      900
gtgcagggca tggcgtcgct gcaggacctg ctgctctcga caacccgct gggcggcggc       960 ctgccgcagt ccggctgggg ggcgctggcg ggcctggcca cgctggacct gtccaacgtc     1020
ggcctcgtgg cgccataccc ggggtccatg gcggccctga cggggctccg gttcctggcg     1080
ctggaccaca accgctgac ggggggccgtg ccgcccgagc tcgcccggct gcccagcatc     1140
ggcgcgctgt acctgaacgg caacaacctg acggggacgc tggagttctc ggccgggttc     1200
taccagcgca tggggcggcg gttcgcgtcg tgggacaacc ccgggctgta ctacaacgtc     1260
gcggccgtgg acgcggccca cgcgccgtcg ggcgtggtgg tgtgcaagga cctgcaggag     1320
cccagcgtgg gcggcggcgc gcgggacggg gacggggacg gggacgcgga ggaggacggg     1380
acgaagcccg aggcgggctc cagcctcgtg gcctcctcgt cgtccggcat gccggttggc     1440
agtgtcggtg ggctccggta cctggtggtg gttcggggaa tggcggctgc ggttcttggg     1500
ttggtgtccc tcctacaata g                                              1521

<210> SEQ ID NO 29
```

```
<211> LENGTH: 38
<212> TYPE: DNA
<213> ORGANISM: Artificial Sequence
<220> FEATURE:
<223> OTHER INFORMATION: Repair template

<400> SEQUENCE: 29
gtcgtgggac aaccccggtc tgtactacaa cgtcgcgg                              38

<210> SEQ ID NO 30
<211> LENGTH: 38
<212> TYPE: DNA
<213> ORGANISM: Artificial Sequence
<220> FEATURE:
<223> OTHER INFORMATION: Repair template

<400> SEQUENCE: 30
gtcgtgggat aacccaggtc tgtactacaa cgtcgcgg                              38

<210> SEQ ID NO 31
<211> LENGTH: 38
<212> TYPE: DNA
<213> ORGANISM: Artificial Sequence
<220> FEATURE:
<223> OTHER INFORMATION: repair template

<400> SEQUENCE: 31
gtcgtgggat aacccagggc tgtactacaa cgtcgcgg                              38

<210> SEQ ID NO 32
<211> LENGTH: 38
<212> TYPE: DNA
<213> ORGANISM: Artificial Sequence
<220> FEATURE:
<223> OTHER INFORMATION: repair template

<400> SEQUENCE: 32
gtcgtgggac aacccagggc tgtactacaa cgtcgcgg                              38

<210> SEQ ID NO 33
<211> LENGTH: 38
<212> TYPE: DNA
<213> ORGANISM: Artificial Sequence
<220> FEATURE:
<223> OTHER INFORMATION: repair template

<400> SEQUENCE: 33
gtcgtgggac aacccagggc tgtactataa cgtagcgg                              38

<210> SEQ ID NO 34
<211> LENGTH: 12
<212> TYPE: PRT
<213> ORGANISM: Zea mays

<400> SEQUENCE: 34

Arg Glu Val Pro Thr Gly Pro Asp Pro Ile His His
1               5                   10

<210> SEQ ID NO 35
<211> LENGTH: 31
<212> TYPE: PRT
<213> ORGANISM: Zea mays

<400> SEQUENCE: 35

Leu Trp Tyr Pro Thr Val Met Ser Ile Gly Pro Val Leu Asp Asn Ser
1               5                   10                  15
```

Leu Gln Cys Gly Pro Asp Ala Lys Phe Ser Ala Gln Leu Phe Asp
            20                  25                  30

<210> SEQ ID NO 36
<211> LENGTH: 31
<212> TYPE: PRT
<213> ORGANISM: Zea mays

<400> SEQUENCE: 36

Leu Arg Arg Leu Arg Thr Leu Ser Phe Tyr Ser Cys Phe Pro Ala Ser
1               5                   10                  15

Asn Pro Thr Ala Ile Pro Thr Gly Ser Trp Glu Lys Leu Ala Gly
            20                  25                  30

<210> SEQ ID NO 37
<211> LENGTH: 24
<212> TYPE: PRT
<213> ORGANISM: Zea mays

<400> SEQUENCE: 37

Thr Leu Glu Thr Leu Glu Phe Arg Thr Asn Pro Gly Leu Asn Gly Ala
1               5                   10                  15

Ile Pro Ala Ser Leu Gly Arg Leu
            20

<210> SEQ ID NO 38
<211> LENGTH: 23
<212> TYPE: PRT
<213> ORGANISM: Zea mays

<400> SEQUENCE: 38

Ala Ser Leu Gln Ser Leu Val Leu Val Glu Asn Asn Leu Thr Gly Pro
1               5                   10                  15

Val Pro Ala Glu Leu Gly Ala
            20

<210> SEQ ID NO 39
<211> LENGTH: 26
<212> TYPE: PRT
<213> ORGANISM: Zea mays

<400> SEQUENCE: 39

Leu Ser Arg Leu Arg Arg Leu Val Leu Ser Gly Asn Gly Leu Ser Gly
1               5                   10                  15

Pro Ile Pro Val Thr Leu Gly Asn Asp Arg
            20                  25

<210> SEQ ID NO 40
<211> LENGTH: 26
<212> TYPE: PRT
<213> ORGANISM: Zea mays

<400> SEQUENCE: 40

Arg Ala Asp Glu Leu Leu Leu Ile Val Asp Leu Ser Arg Asn Tyr Leu
1               5                   10                  15

Thr Gly Ser Leu Pro Ser Ser Leu Gly Gly
            20                  25

<210> SEQ ID NO 41
<211> LENGTH: 24
<212> TYPE: PRT
<213> ORGANISM: Zea mays

```
<400> SEQUENCE: 41

Leu Thr Gly Leu Leu Lys Met Asp Leu Ser Ser Asn Leu Leu Gln Gly
1               5                   10                  15

Ser Ile Pro Pro Glu Leu Ala Gly
            20

<210> SEQ ID NO 42
<211> LENGTH: 24
<212> TYPE: PRT
<213> ORGANISM: Zea mays

<400> SEQUENCE: 42

Leu Arg Ser Leu Thr Leu Leu Asp Leu Arg Asn Asn Ser Leu Thr Gly
1               5                   10                  15

Gly Leu Pro Gln Phe Val Gln Gly
            20

<210> SEQ ID NO 43
<211> LENGTH: 25
<212> TYPE: PRT
<213> ORGANISM: Zea mays

<400> SEQUENCE: 43

Met Ala Ser Leu Gln Asp Leu Leu Ser Asn Asn Pro Leu Gly Gly
1               5                   10                  15

Gly Leu Pro Gln Ser Gly Trp Gly Ala
            20                  25

<210> SEQ ID NO 44
<211> LENGTH: 24
<212> TYPE: PRT
<213> ORGANISM: Zea mays

<400> SEQUENCE: 44

Leu Ala Gly Leu Ala Thr Leu Asp Leu Ser Asn Val Gly Leu Val Gly
1               5                   10                  15

Ala Ile Pro Gly Ser Met Ala Ala
            20

<210> SEQ ID NO 45
<211> LENGTH: 25
<212> TYPE: PRT
<213> ORGANISM: Zea mays

<400> SEQUENCE: 45

Leu Thr Gly Leu Arg Phe Leu Ala Leu Asp His Asn Arg Leu Thr Gly
1               5                   10                  15

Ala Val Pro Pro Glu Leu Ala Arg Leu
            20                  25

<210> SEQ ID NO 46
<211> LENGTH: 28
<212> TYPE: PRT
<213> ORGANISM: Zea mays

<400> SEQUENCE: 46

Pro Ser Ile Gly Ala Leu Tyr Leu Asn Gly Asn Asn Leu Thr Gly Thr
1               5                   10                  15

Leu Glu Phe Ser Ala Gly Phe Tyr Gln Arg Met Gly
            20                  25
```